(12) United States Patent
Brass et al.

(10) Patent No.: US 8,735,099 B2
(45) Date of Patent: May 27, 2014

(54) MELIBIOSE OPERON EXPRESSION SYSTEM

(75) Inventors: Johann Brass, Ausserberg (CH); Joachim Klein, Visp (CH); Ralf Ostendorp, Munich (DE)

(73) Assignee: Morphosys AG, Martinsried/Planegg (DE)

( * ) Notice: Subject to any disclaimer, the term of this patent is extended or adjusted under 35 U.S.C. 154(b) by 0 days.

(21) Appl. No.: 13/064,928

(22) Filed: Apr. 27, 2011

(65) Prior Publication Data

US 2012/0077225 A1    Mar. 29, 2012

Related U.S. Application Data

(63) Continuation of application No. 11/791,988, filed as application No. PCT/EP2005/013012 on Dec. 5, 2005, now abandoned.

(30) Foreign Application Priority Data

Dec. 7, 2004  (EP) .................................... 04028920

(51) Int. Cl.
   *C12P 21/02*  (2006.01)
   *C12N 15/00*  (2006.01)
   *C07H 21/04*  (2006.01)
(52) U.S. Cl.
   USPC ..................... 435/71.2; 435/320.1; 536/23.1
(58) Field of Classification Search
   None
   See application file for complete search history.

(56) References Cited

U.S. PATENT DOCUMENTS

| 5,843,703 | A | * | 12/1998 | Campbell et al. | ............ 435/69.1 |
| 5,849,576 | A | * | 12/1998 | Skerra et al. | ............... 435/320.1 |
| 6,083,715 | A | * | 7/2000 | Georgiou et al. | ............ 435/69.1 |
| 7,425,429 | B2 | * | 9/2008 | Bumann | ..................... 435/69.1 |

OTHER PUBLICATIONS

Belyaeva et al., Mol. Microbiol. 36(1): 211-222, 2000.*

* cited by examiner

*Primary Examiner* — Nancy T Vogel
(74) *Attorney, Agent, or Firm* — Hoffmann & Baron LLP

(57) ABSTRACT

New vectors expressible in a host comprising the promoter region of the melibiose operon operably linked to a transcriptional unit that includes nucleic acid sequence which is heterologous to the host. The expression of the nucleic acid sequence is controlled by the promoter region of the melibiose operon. The new vector can be used for the regulated heterologous expression of a nucleic acid sequence in a prokaryotic host. There is an isolated and purified nucleic acid sequence expressible in a host comprising the promoter region of the melibiose operon operably linked to a transcriptional unit that includes a nucleic acid sequence which is heterologous to the host. The expression of the nucleic acid sequence is controlled by the promoter region of the melibiose operon. A prokaryotic host is transformed with the vector or the isolated and purified nucleic acid sequence. There is a method for producing a polypeptide in a host using the vector.

16 Claims, 10 Drawing Sheets

SEQUENCE LISTING

```
<160> NUMBER OF SEQ ID NOS: 71

<210> SEQ ID NO 1
<211> LENGTH: 143
<212> TYPE: DNA
<213> ORGANISM: Escherichia coli

<400> SEQUENCE: 1
actctgcttt tcaggtaatt tattcccata aactcagatt tactgctgct tcacgcagga      60
tctgagttta tgggaatgct caacctggaa gccggaggtt ttctgcagat tcgcctgcca     120
tgatgaagtt attcaagcaa gcc                                             143

<210> SEQ ID NO 2
<211> LENGTH: 13
<212> TYPE: DNA
<213> ORGANISM: Escherichia coli

<400> SEQUENCE: 2
aggagatata cat                                                         13

<210> SEQ ID NO 3
<211> LENGTH: 1630
<212> TYPE: DNA
<213> ORGANISM: Escherichia coli

<400> SEQUENCE: 3
atcgatactc tgcttttcag gtaatttatt cccataaact cagatttact gctgcttcac      60
gcaggatctg agtttatggg aatgctcaac ctggaagccg gaggttttct gcagattcgc     120
ctgccatgat gaagttattc aagcaagccc ttaagaagga gatatacata tgaaaaagac     180
agctatcgcg attgcagtgg cactggctgg tttcgctacc gtagcgcagg ccgatatcga     240
actgacccag ccgccttcag tgagcgttgc accaggtcag accgcgcgta tctcgtgtag     300
cggcgatgcg ctgggcgata aatacgcgag ctggtaccag cagaaacccg ggcaggcgcc     360
agttctggtg atttatgatg attctgaccg tccctcaggc atcccggaac gctttagcgg     420
atccaacagc ggcaacaccg cgaccctgac cattagcggc actcaggcgg aagacgaagc     480
ggattattat tgccagagct atgactctcc tcaggttgtg tttggcggcg gcacgaagtt     540
```

```
aaccgttctt ggccagccga aagccgcacc gagtgtgacg ctgtttccgc cgagcagcga      600
agaattgcag gcgaacaaag cgaccctggt gtgcctgatt agcgactttt atccgggagc      660
cgtgacagtg gcctggaagg cagatagcag ccccgtcaag gcgggagtgg agaccaccac      720
accctccaaa caaagcaaca caagtacgc ggccagcagc tatctgagcc tgacgcctga      780
gcagtggaag tcccacagaa gctacagctg ccaggtcacg catgagggga gcaccgtgga      840
aaaaaccgtt gcgccgactg aggcctgata agcatgcgta ggagaaaata aaatgaaaca      900
aagcactatt gcactggcac tcttaccgtt gctcttcacc cctgttacca aagcccaggt      960
gcaattgaaa gaaagcggcc cggccctggt gaaaccgacc caaaccctga ccctgacctg     1020
taccttttcc ggatttagcc tgtccacgtc tggcgttggc gtgggctgga ttcgccagcc     1080
gcctgggaaa gccctcgagt ggctggctct gattgattgg gatgatgata agtattatag     1140
caccagcctg aaaacgcgtc tgaccattag caaagatact tcgaaaaatc aggtggtgct     1200
gactatgacc aacatggacc cggtggatac ggccacctat tattgcgcgc gttatcctgt     1260
tactcagcgt tcttatatgg atgtttgggg ccaaggcacc ctggtgacgg ttagctcagc     1320
gtcgaccaaa ggtccaagcg tgtttccgct ggctccgagc agcaaaagca ccagcggcgg     1380
cacggctgcc ctgggctgcc tggttaaaga ttatttcccg gaaccagtca ccgtgagctg     1440
gaacagcggg gcgctgacca gcggcgtgca taccttccg gcggtgctgc aaagcagcgg     1500
cctgtatagc ctgagcagcg ttgtgaccgt gccgagcagc agcttaggca ctcagaccta     1560
tatttgcaac gtgaaccata aaccgagcaa caccaaagtg gataaaaaag tggaaccgaa     1620
aagctgataa                                                           1630
```

<210> SEQ ID NO 4
<211> LENGTH: 1659
<212> TYPE: DNA
<213> ORGANISM: Escherichia coli

<400> SEQUENCE: 4

```
atcgatactc tgcttttcag gtaatttatt cccataaact cagatttact gctgcttcac       60
gcaggatctg agtttatggg aatgctcaac ctggaagccg gaggttttct gcagattcgc      120
ctgccatgat gaagttattc aagcaagccc ttaagaagga gatatacata tgatgattac      180
tctgcgcaaa cttcctctgg cggttgccgt cgcagcgggc gtaatgtctg ctcaggcaat      240
ggctgatatc gaactgaccc agccgccttc agtgagcgtt gcaccaggtc agaccgcgcg      300
tatctcgtgt agcggcgatg cgctgggcga taaatacgcg agctggtacc agcagaaacc      360
cgggcaggcg ccagttctgg tgatttatga tgattctgac cgtccctcag gcatcccgga      420
acgctttagc ggatccaaca gcggcaacac cgcgaccctg accattagcg gcactcaggc      480
ggaagacgaa gcggattatt attgccagag ctatgactct cctcaggttg tgtttggcgg      540
cggcacgaag ttaaccgttc ttggccagcc gaaagccgca ccgagtgtga cgctgtttcc      600
gccgagcagc gaagaattgc aggcgaacaa agcgaccctg gtgtgcctga ttagcgactt      660
ttatccggga gccgtgacag tggcctggaa ggcagatagc agccccgtca aggcgggagt      720
ggagaccacc acaccctcca aacaaagcaa caacaagtac gcggccagca gctatctgag      780
cctgacgcct gagcagtgga gtcccacag aagctacagc tgccaggtca cgcatgaggg      840
gagcaccgtg gaaaaaaccg ttgcgccgac tgaggcctga taactgcagg agatatacat      900
atgaaaataa aacaggtgc acgcatcctc gcattatccg cattaacgac gatgatgttt      960
tccgcctcgg ctctcgccca ggtgcaattg aaagaaagcg gccggccct ggtgaaaccg     1020
```

-continued

```
acccaaaccc tgaccctgac ctgtacctttt tccggattta gcctgtccac gtctggcgtt    1080
ggcgtgggct ggattcgcca gccgcctggg aaagccctcg agtggctggc tctgattgat    1140
tgggatgatg ataagtatta tagcaccagc ctgaaaacgc gtctgaccat tagcaaagat    1200
acttcgaaaa atcaggtggt gctgactatg accaacatgg acccggtgga tacggccacc    1260
tattattgcg cgcgttatcc tgttactcag cgttcttata tggatgtttg gggccaaggc    1320
accctggtga cggttagctc agcgtcgacc aaaggtccaa gcgtgtttcc gctggctccg    1380
agcagcaaaa gcaccagcgg cggcacggct gccctgggct gcctggttaa agattatttc    1440
ccggaaccag tcaccgtgag ctggaacagc ggggcgctga ccagcggcgt gcatacctttt    1500 ccggcggtgc tgcaaagcag cggcctgtat agcctgagca gcgttgtgac cgtgccgagc    1560
agcagcttag gcactcagac ctatatttgc aacgtgaacc ataaaccgag caacaccaaa    1620
gtggataaaa aagtggaacc gaaaagctga taaaagctt                            1659
```

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
aaaatcgata aatgaaacgc atatttg                                          27

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
aaacttaagt tgttatcaac ttgttat                                          27

<210> SEQ ID NO 7
<211> LENGTH: 154
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
aaaatcgata actgaaacgc atatttgcgg attagttcat gactttatct ctaacaaatt     60
gaaattaaac atttaattttt attaaggcaa ttgtggcaca ccccttgctt tgtctttatc    120
aacgcaaata acaagttgat aacaacttaa gttt                                 154

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
aaaatcgatg catcacgccc cgcacaa                                          27

<210> SEQ ID NO 9

```
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
aaacttaagt caggatttat tgtttta                                          27

<210> SEQ ID NO 10
<211> LENGTH: 218
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
aaaatcgatg catcacgccc cgcacaagga agcggtagtc actgcccgat acggacttta     60
cataactcaa ctcattcccc tcgctatcct tttattcaaa ctttcaaatt aaaatattta    120
tctttcattt tgcgatcaaa ataacacttt taaatctttc aatctgatta gattaggttg    180
ccgtttggta ataaaacaat aaatcctgac ttaagttt                            218

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
aaaatcgatg actgcgagtg ggagcac                                         27

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
aaacttaagg gcttgcttga ataactt                                         27

<210> SEQ ID NO 13
<211> LENGTH: 161
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
aaaatcgata ctctgctttt caggtaattt attcccataa actcagattt actgctgctt     60
cacgcaggat ctgagtttat gggaatgctc aacctggaag ccggaggttt tctgcagatt    120
cgcctgccat gatgaagtta ttcaagcaag cccttaagtt t                        161

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
```

-continued primer

<400> SEQUENCE: 14
aaacatatga aaaagacagc tatc                                           24

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
aaaaagcttt tatcagcttt tcggttc                                        27

<210> SEQ ID NO 16
<211> LENGTH: 26
<212> TYPE: PRT
<213> ORGANISM: Escherichia coli

<400> SEQUENCE: 16

Met Lys Lys Thr Ala Ile Ala Ile Ala Val Ala Leu Ala Gly Phe Ala
1               5                   10                  15

Thr Val Ala Gln Ala Ala Pro Lys Asp Asn
            20                  25

<210> SEQ ID NO 17
<211> LENGTH: 26
<212> TYPE: PRT
<213> ORGANISM: Escherichia coli

<400> SEQUENCE: 17

Met Lys Lys Thr Ala Ile Ala Ile Ala Val Ala Leu Ala Gly Phe Ala
1               5                   10                  15

Thr Val Ala Gln Ala Asp Ile Glu Leu Thr
            20                  25

<210> SEQ ID NO 18
<211> LENGTH: 26
<212> TYPE: PRT
<213> ORGANISM: Escherichia coli

<400> SEQUENCE: 18

Val Lys Gln Ser Thr Ile Ala Leu Ala Leu Leu Pro Leu Leu Phe Thr
1               5                   10                  15

Pro Val Thr Lys Ala Arg Thr Pro Glu Met
            20                  25

<210> SEQ ID NO 19
<211> LENGTH: 26
<212> TYPE: PRT
<213> ORGANISM: Escherichia coli

<400> SEQUENCE: 19

Met Lys Gln Ser Thr Ile Ala Leu Ala Leu Leu Pro Leu Leu Phe Thr
1               5                   10                  15

Pro Val Thr Lys Ala Gln Val Gln Leu Lys
            20                  25

<210> SEQ ID NO 20
<211> LENGTH: 27
<212> TYPE: PRT
<213> ORGANISM: Erwinia chrysanthemi -continued

```
<400> SEQUENCE: 20

Met Lys Ser Leu Ile Thr Pro Ile Thr Ala Gly Leu Leu Ala Leu
 1               5                  10                  15

Ser Gln Pro Leu Leu Ala Ala Thr Asp Thr Gly
            20                  25

<210> SEQ ID NO 21
<211> LENGTH: 27
<212> TYPE: PRT
<213> ORGANISM: Erwinia chrysanthemi

<400> SEQUENCE: 21

Met Lys Ser Leu Ile Thr Pro Ile Thr Ala Gly Leu Leu Ala Leu
 1               5                  10                  15

Ser Gln Pro Leu Leu Ala Asp Ile Glu Leu Thr
            20                  25

<210> SEQ ID NO 22
<211> LENGTH: 27
<212> TYPE: PRT
<213> ORGANISM: Erwinia chrysanthemi

<400> SEQUENCE: 22

Met Lys Ser Leu Ile Thr Pro Ile Thr Ala Gly Leu Leu Ala Leu
 1               5                  10                  15

Ser Gln Pro Leu Leu Ala Gln Val Gln Leu Lys
            20                  25

<210> SEQ ID NO 23
<211> LENGTH: 27
<212> TYPE: PRT
<213> ORGANISM: Erwinia carotovora

<400> SEQUENCE: 23

Met Lys Tyr Leu Leu Pro Thr Ala Ala Ala Gly Leu Leu Leu Ala
 1               5                  10                  15

Ala Gln Pro Ala Met Ala Ala Asn Thr Gly Gly
            20                  25

<210> SEQ ID NO 24
<211> LENGTH: 27
<212> TYPE: PRT
<213> ORGANISM: Erwinia carotovora

<400> SEQUENCE: 24

Met Lys Tyr Leu Leu Pro Thr Ala Ala Ala Gly Leu Leu Leu Ala
 1               5                  10                  15

Ala Gln Pro Ala Met Ala Asp Ile Glu Leu Thr
            20                  25

<210> SEQ ID NO 25
<211> LENGTH: 27
<212> TYPE: PRT
<213> ORGANISM: Erwinia carotovora

<400> SEQUENCE: 25

Met Lys Tyr Leu Leu Pro Thr Ala Ala Ala Gly Leu Leu Leu Ala
 1               5                  10                  15

Ala Gln Pro Ala Met Ala Gln Val Gln Leu Lys
            20                  25
```

```
<210> SEQ ID NO 26
<211> LENGTH: 31
<212> TYPE: PRT
<213> ORGANISM: Xanthomonas campestris

<400> SEQUENCE: 26

Met Lys Pro Lys Phe Ser Thr Ala Ala Ala Ser Leu Phe Val Gly
  1               5                  10                  15

Ser Leu Leu Val Ile Gly Val Ala Ser Ala Asp Pro Ala Leu Glu
                 20                  25                  30

<210> SEQ ID NO 27
<211> LENGTH: 31
<212> TYPE: PRT
<213> ORGANISM: Xanthomonas campestris

<400> SEQUENCE: 27

Met Lys Pro Lys Phe Ser Thr Ala Ala Ala Ser Leu Phe Val Gly
  1               5                  10                  15

Ser Leu Leu Val Ile Gly Val Ala Ser Ala Asp Ile Glu Leu Thr
                 20                  25                  30

<210> SEQ ID NO 28
<211> LENGTH: 31
<212> TYPE: PRT
<213> ORGANISM: Xanthomonas campestris

<400> SEQUENCE: 28

Met Lys Pro Lys Phe Ser Thr Ala Ala Ala Ser Leu Phe Val Gly
  1               5                  10                  15

Ser Leu Leu Val Ile Gly Val Ala Ser Ala Gln Val Gln Leu Lys
                 20                  25                  30

<210> SEQ ID NO 29
<211> LENGTH: 30
<212> TYPE: PRT
<213> ORGANISM: Escherichia coli

<400> SEQUENCE: 29

Met Met Ile Thr Leu Arg Lys Leu Pro Leu Ala Val Ala Val Ala Ala
  1               5                  10                  15

Gly Val Met Ser Ala Gln Ala Met Ala Val Asp Phe His Gly
                 20                  25                  30

<210> SEQ ID NO 30
<211> LENGTH: 30
<212> TYPE: PRT
<213> ORGANISM: Escherichia coli

<400> SEQUENCE: 30

Met Met Ile Thr Leu Arg Lys Leu Pro Leu Ala Val Ala Val Ala Ala
  1               5                  10                  15

Gly Val Met Ser Ala Gln Ala Met Ala Asp Ile Glu Leu Thr
                 20                  25                  30

<210> SEQ ID NO 31
<211> LENGTH: 30
<212> TYPE: PRT
<213> ORGANISM: Escherichia coli

<400> SEQUENCE: 31

Met Met Ile Thr Leu Arg Lys Leu Pro Leu Ala Val Ala Val Ala Ala
  1               5                  10                  15
```

```
Gly Val Met Ser Ala Gln Ala Met Ala Gln Val Gln Leu Lys
            20                  25                  30

<210> SEQ ID NO 32
<211> LENGTH: 31
<212> TYPE: PRT
<213> ORGANISM: Escherichia coli

<400> SEQUENCE: 32

Met Lys Ile Lys Thr Gly Ala Arg Ile Leu Ala Leu Ser Ala Leu Thr
 1               5                  10                  15

Thr Met Met Phe Ser Ala Ser Ala Leu Ala Lys Ile Glu Glu Gly
            20                  25                  30

<210> SEQ ID NO 33
<211> LENGTH: 31
<212> TYPE: PRT
<213> ORGANISM: Escherichia coli

<400> SEQUENCE: 33

Met Lys Ile Lys Thr Gly Ala Arg Ile Leu Ala Leu Ser Ala Leu Thr
 1               5                  10                  15

Thr Met Met Phe Ser Ala Ser Ala Leu Ala Asp Ile Glu Leu Thr
            20                  25                  30

<210> SEQ ID NO 34
<211> LENGTH: 31
<212> TYPE: PRT
<213> ORGANISM: Escherichia coli

<400> SEQUENCE: 34

Met Lys Ile Lys Thr Gly Ala Arg Ile Leu Ala Leu Ser Ala Leu Thr
 1               5                  10                  15

Thr Met Met Phe Ser Ala Ser Ala Leu Ala Gln Val Gln Leu Lys
            20                  25                  30

<210> SEQ ID NO 35
<211> LENGTH: 28
<212> TYPE: PRT
<213> ORGANISM: Escherichia coli

<400> SEQUENCE: 35

Met Ser Ile Gln His Phe Arg Val Ala Leu Ile Pro Phe Phe Ala Ala
 1               5                  10                  15

Phe Cys Leu Pro Val Phe Ala His Pro Glu Thr Leu
            20                  25

<210> SEQ ID NO 36
<211> LENGTH: 28
<212> TYPE: PRT
<213> ORGANISM: Escherichia coli

<400> SEQUENCE: 36

Met Ser Ile Gln His Phe Arg Val Ala Leu Ile Pro Phe Phe Ala Ala
 1               5                  10                  15

Phe Cys Leu Pro Val Phe Ala Asp Ile Glu Leu Thr
            20                  25

<210> SEQ ID NO 37
<211> LENGTH: 28
<212> TYPE: PRT
<213> ORGANISM: Escherichia coli

<400> SEQUENCE: 37
```

```
Met Ser Ile Gln His Phe Arg Val Ala Leu Ile Pro Phe Phe Ala Ala
1               5                   10                  15
Phe Cys Leu Pro Val Phe Ala Gln Val Gln Leu Lys
                20                  25
```

<210> SEQ ID NO 38
<211> LENGTH: 31
<212> TYPE: PRT
<213> ORGANISM: Escherichia coli

<400> SEQUENCE: 38

```
Met Thr Asn Ile Thr Lys Arg Ser Leu Val Ala Ala Gly Val Leu Ala
1               5                   10                  15
Ala Leu Met Ala Gly Asn Val Ala Leu Ala Ala Asp Val Pro Ala
                20                  25                  30
```

<210> SEQ ID NO 39
<211> LENGTH: 31
<212> TYPE: PRT
<213> ORGANISM: Escherichia coli

<400> SEQUENCE: 39

```
Met Thr Asn Ile Thr Lys Arg Ser Leu Val Ala Ala Gly Val Leu Ala
1               5                   10                  15
Ala Leu Met Ala Gly Asn Val Ala Leu Ala Asp Ile Glu Leu Thr
                20                  25                  30
```

<210> SEQ ID NO 40
<211> LENGTH: 31
<212> TYPE: PRT
<213> ORGANISM: Escherichia coli

<400> SEQUENCE: 40

```
Met Thr Asn Ile Thr Lys Arg Ser Leu Val Ala Ala Gly Val Leu Ala
1               5                   10                  15
Ala Leu Met Ala Gly Asn Val Ala Leu Ala Gln Val Gln Leu Lys
                20                  25                  30
```

<210> SEQ ID NO 41
<211> LENGTH: 35
<212> TYPE: PRT
<213> ORGANISM: Escherichia coli

<400> SEQUENCE: 41

```
Met Lys Ser Pro Ala Pro Ser Arg Pro Gln Lys Met Ala Leu Ile Pro
1               5                   10                  15
Ala Cys Ile Phe Leu Cys Phe Ala Ala Leu Ser Val Gln Ala Glu Glu
                20                  25                  30
Thr Pro Val
        35
```

<210> SEQ ID NO 42
<211> LENGTH: 35
<212> TYPE: PRT
<213> ORGANISM: Escherichia coli

<400> SEQUENCE: 42

```
Met Lys Ser Pro Ala Pro Ser Arg Pro Gln Lys Met Ala Leu Ile Pro
1               5                   10                  15
Ala Cys Ile Phe Leu Cys Phe Ala Ala Leu Ser Val Gln Ala Asp Ile
                20                  25                  30
```

```
Glu Leu Thr
        35

<210> SEQ ID NO 43
<211> LENGTH: 35
<212> TYPE: PRT
<213> ORGANISM: Escherichia coli

<400> SEQUENCE: 43

Met Lys Ser Pro Ala Pro Ser Arg Pro Gln Lys Met Ala Leu Ile Pro
1               5                   10                  15

Ala Cys Ile Phe Leu Cys Phe Ala Ala Leu Ser Val Gln Ala Gln Val
            20                  25                  30

Gln Leu Lys
        35

<210> SEQ ID NO 44
<211> LENGTH: 27
<212> TYPE: PRT
<213> ORGANISM: Escherichia coli

<400> SEQUENCE: 44

Met Lys His Ser Val Ser Val Thr Cys Cys Ala Leu Leu Val Ser Ser
1               5                   10                  15

Ile Ser Leu Ser Tyr Ala Ala Glu Val Pro Ser
            20                  25

<210> SEQ ID NO 45
<211> LENGTH: 27
<212> TYPE: PRT
<213> ORGANISM: Escherichia coli

<400> SEQUENCE: 45

Met Lys His Ser Val Ser Val Thr Cys Cys Ala Leu Leu Val Ser Ser
1               5                   10                  15

Ile Ser Leu Ser Tyr Ala Asp Ile Glu Leu Thr
            20                  25

<210> SEQ ID NO 46
<211> LENGTH: 27
<212> TYPE: PRT
<213> ORGANISM: Escherichia coli

<400> SEQUENCE: 46

Met Lys His Ser Val Ser Val Thr Cys Cys Ala Leu Leu Val Ser Ser
1               5                   10                  15

Ile Ser Leu Ser Tyr Ala Gln Val Gln Leu Lys
            20                  25

<210> SEQ ID NO 47
<211> LENGTH: 25
<212> TYPE: PRT
<213> ORGANISM: Escherichia coli

<400> SEQUENCE: 47

Met Lys Trp Leu Cys Ser Val Gly Ile Ala Val Ser Leu Ala Leu Gln
1               5                   10                  15

Pro Ala Leu Ala Asp Asp Leu Phe Gly
            20                  25

<210> SEQ ID NO 48
<211> LENGTH: 25
<212> TYPE: PRT
```

```
<213> ORGANISM: Escherichia coli

<400> SEQUENCE: 48

Met Lys Trp Leu Cys Ser Val Gly Ile Ala Val Ser Leu Ala Leu Gln
1               5                   10                  15

Pro Ala Leu Ala Asp Ile Glu Leu Thr
            20                  25

<210> SEQ ID NO 49
<211> LENGTH: 25
<212> TYPE: PRT
<213> ORGANISM: Escherichia coli

<400> SEQUENCE: 49

Met Lys Trp Leu Cys Ser Val Gly Ile Ala Val Ser Leu Ala Leu Gln
1               5                   10                  15

Pro Ala Leu Ala Gln Val Gln Leu Lys
            20                  25

<210> SEQ ID NO 50
<211> LENGTH: 27
<212> TYPE: PRT
<213> ORGANISM: Escherichia coli

<400> SEQUENCE: 50

Met Lys Lys Ser Ile Leu Ala Leu Ser Leu Leu Val Gly Leu Ser Thr
1               5                   10                  15

Ala Ala Ser Ser Tyr Ala Ala Leu Pro Glu Thr
            20                  25

<210> SEQ ID NO 51
<211> LENGTH: 27
<212> TYPE: PRT
<213> ORGANISM: Escherichia coli

<400> SEQUENCE: 51

Met Lys Lys Ser Ile Leu Ala Leu Ser Leu Leu Val Gly Leu Ser Thr
1               5                   10                  15

Ala Ala Ser Ser Tyr Ala Asp Ile Glu Leu Thr
            20                  25

<210> SEQ ID NO 52
<211> LENGTH: 27
<212> TYPE: PRT
<213> ORGANISM: Escherichia coli

<400> SEQUENCE: 52

Met Lys Lys Ser Ile Leu Ala Leu Ser Leu Leu Val Gly Leu Ser Thr
1               5                   10                  15

Ala Ala Ser Ser Tyr Ala Gln Val Gln Leu Lys
            20                  25

<210> SEQ ID NO 53
<211> LENGTH: 22
<212> TYPE: PRT
<213> ORGANISM: Escherichia coli

<400> SEQUENCE: 53

Met Lys Leu Ala Ala Cys Phe Leu Thr Leu Leu Pro Gly Phe Ala Val
1               5                   10                  15

Ala Ala Ser Trp Thr Ser
            20
```

```
<210> SEQ ID NO 54
<211> LENGTH: 22
<212> TYPE: PRT
<213> ORGANISM: Escherichia coli

<400> SEQUENCE: 54

Met Lys Leu Ala Ala Cys Phe Leu Thr Leu Leu Pro Gly Phe Ala Val
 1               5                  10                  15

Ala Asp Ile Glu Leu Thr
            20

<210> SEQ ID NO 55
<211> LENGTH: 22
<212> TYPE: PRT
<213> ORGANISM: Escherichia coli

<400> SEQUENCE: 55

Met Lys Leu Ala Ala Cys Phe Leu Thr Leu Leu Pro Gly Phe Ala Val
 1               5                  10                  15

Ala Gln Val Gln Leu Lys
            20

<210> SEQ ID NO 56
<211> LENGTH: 27
<212> TYPE: PRT
<213> ORGANISM: Escherichia coli

<400> SEQUENCE: 56

Met Lys Lys Leu Val Leu Ser Leu Ser Leu Val Leu Ala Phe Ser Ser
 1               5                  10                  15

Ala Thr Ala Ala Phe Ala Ala Ile Pro Gln Asn
            20                  25

<210> SEQ ID NO 57
<211> LENGTH: 27
<212> TYPE: PRT
<213> ORGANISM: Escherichia coli

<400> SEQUENCE: 57

Met Lys Lys Leu Val Leu Ser Leu Ser Leu Val Leu Ala Phe Ser Ser
 1               5                  10                  15

Ala Thr Ala Ala Phe Ala Asp Ile Glu Leu Thr
            20                  25

<210> SEQ ID NO 58
<211> LENGTH: 27
<212> TYPE: PRT
<213> ORGANISM: Escherichia coli

<400> SEQUENCE: 58

Met Lys Lys Leu Val Leu Ser Leu Ser Leu Val Leu Ala Phe Ser Ser
 1               5                  10                  15

Ala Thr Ala Ala Phe Ala Gln Val Gln Leu Lys
            20                  25

<210> SEQ ID NO 59
<211> LENGTH: 28
<212> TYPE: PRT
<213> ORGANISM: Escherichia coli

<400> SEQUENCE: 59

Met Lys Ile Lys Asn Ile Leu Leu Thr Leu Cys Thr Ser Leu Leu Leu
 1               5                  10                  15
```

Thr Asn Val Ala Ala His Ala Lys Glu Val Lys Ile
            20                  25

<210> SEQ ID NO 60
<211> LENGTH: 28
<212> TYPE: PRT
<213> ORGANISM: Escherichia coli

<400> SEQUENCE: 60

Met Lys Ile Lys Asn Ile Leu Leu Thr Leu Cys Thr Ser Leu Leu Leu
 1               5                  10                  15

Thr Asn Val Ala Ala His Ala Asp Ile Glu Leu Thr
            20                  25

<210> SEQ ID NO 61
<211> LENGTH: 28
<212> TYPE: PRT
<213> ORGANISM: Escherichia coli

<400> SEQUENCE: 61

Met Lys Ile Lys Asn Ile Leu Leu Thr Leu Cys Thr Ser Leu Leu Leu
 1               5                  10                  15

Thr Asn Val Ala Ala His Ala Gln Val Gln Leu Lys
            20                  25

<210> SEQ ID NO 62
<211> LENGTH: 26
<212> TYPE: PRT
<213> ORGANISM: Escherichia coli

<400> SEQUENCE: 62

Met Leu Ala Phe Ile Arg Phe Leu Phe Ala Gly Leu Leu Leu Val Ile
 1               5                  10                  15

Ser His Ala Phe Ala Ala Thr Val Gln Asp
            20                  25

<210> SEQ ID NO 63
<211> LENGTH: 26
<212> TYPE: PRT
<213> ORGANISM: Escherichia coli

<400> SEQUENCE: 63

Met Leu Ala Phe Ile Arg Phe Leu Phe Ala Gly Leu Leu Leu Val Ile
 1               5                  10                  15

Ser His Ala Phe Ala Asp Ile Glu Leu Thr
            20                  25

<210> SEQ ID NO 64
<211> LENGTH: 26
<212> TYPE: PRT
<213> ORGANISM: Escherichia coli

<400> SEQUENCE: 64

Met Leu Ala Phe Ile Arg Phe Leu Phe Ala Gly Leu Leu Leu Val Ile
 1               5                  10                  15

Ser His Ala Phe Ala Gln Val Gln Leu Lys
            20                  25

<210> SEQ ID NO 65
<211> LENGTH: 14
<212> TYPE: DNA
<213> ORGANISM: Artificial Sequence
<220> FEATURE:

-continued

<210> SEQ ID NO 66
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 66
aggagaaaat aaaatg                                                      16

<210> SEQ ID NO 67
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 67
aggagatata catatg                                                      16

<210> SEQ ID NO 68
<211> LENGTH: 236
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 68

Met Met Ile Thr Leu Arg Lys Leu Pro Leu Ala Val Ala Val Ala Ala
 1               5                  10                  15

Gly Val Met Ser Ala Gln Ala Met Ala Asp Ile Glu Leu Thr Gln Pro
             20                  25                  30

Pro Ser Val Ser Val Ala Pro Gly Gln Thr Ala Arg Ile Ser Cys Ser
         35                  40                  45

Gly Asn Ala Leu Gly Asp Lys Tyr Ala Ser Trp Tyr Gln Gln Asn Pro
     50                  55                  60

Gly Gln Ala Pro Val Leu Val Ile Tyr Asp Asp Ser Asp Arg Pro Ser
 65                  70                  75                  80

Gly Ile Pro Glu Arg Phe Ser Gly Ser Asn Ser Gly Asn Thr Ala Thr
                 85                  90                  95

Leu Thr Ile Ser Gly Thr Gln Ala Glu Asp Glu Ala Asp Tyr Tyr Cys
            100                 105                 110

Gln Ser Tyr Asp Ser Pro Gln Val Val Phe Gly Gly Gly Thr Lys Leu
        115                 120                 125

Thr Val Leu Gly Gln Pro Lys Ala Ala Pro Ser Val Thr Leu Phe Pro
    130                 135                 140

Pro Ser Glu Glu Leu Gln Ala Asn Lys Ala Thr Leu Val Cys Leu
145                 150                 155                 160

Ile Ser Asp Phe Tyr Pro Gly Ala Val Thr Val Ala Trp Lys Ala Asp
                165                 170                 175

Ser Ser Pro Val Lys Ala Gly Val Glu Thr Thr Thr Pro Ser Lys Gln
            180                 185                 190

```
Ser Asn Asn Lys Tyr Ala Ala Ser Ser Tyr Leu Ser Leu Thr Pro Glu
        195                 200                 205

Gln Trp Lys Ser His Arg Ser Tyr Ser Cys Gln Val Thr His Glu Gly
    210                 215                 220

Ser Thr Val Glu Lys Thr Val Ala Pro Thr Glu Ala
225                 230                 235

<210> SEQ ID NO 69
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Met Lys Ile Lys Thr Gly Ala Arg Ile Leu Ala Leu Ser Ala Leu Thr
1               5                   10                  15

Thr Met Met Phe Ser Ala Ser Ala Leu Ala Gln Val Gln Leu Lys Glu
            20                  25                  30

Ser Gly Pro Ala Leu Val Lys Pro Thr Gln Thr Leu Thr Leu Thr Cys
        35                  40                  45

Thr Phe Ser Gly Phe Ser Leu Ser Thr Ser Gly Val Gly Val Gly Trp
    50                  55                  60

Ile Arg Gln Pro Pro Gly Lys Ala Leu Glu Trp Leu Ala Leu Ile Asp
65                  70                  75                  80

Trp Asp Asp Asp Lys Tyr Tyr Ser Thr Ser Leu Lys Thr Arg Leu Thr
                85                  90                  95

Ile Ser Lys Asp Thr Ser Lys Asn Gln Val Val Leu Thr Met Thr Asn
            100                 105                 110

Met Asp Pro Val Asp Thr Ala Thr Tyr Tyr Cys Ala Arg Tyr Pro Val
        115                 120                 125

Thr Gln Arg Ser Tyr Met Asp Val Trp Gly Gly Thr Leu Val Thr
    130                 135                 140

Val Ser Ser Ala Ser Thr Lys Gly Pro Ser Val Leu Pro Leu Ala Pro
145                 150                 155                 160

Ser Ser Lys Ser Thr Ser Gly Gly Thr Ala Ala Leu Gly Cys Leu Val
                165                 170                 175

Lys Asp Tyr Phe Pro Glu Pro Val Thr Val Ser Trp Asn Ser Gly Ala
            180                 185                 190

Leu Thr Ser Gly Val His Thr Phe Pro Ala Val Leu Gln Ser Ser Gly
        195                 200                 205

Leu Tyr Ser Leu Ser Ser Val Val Thr Val Pro Ser Ser Ser Leu Gly
    210                 215                 220

Thr Gln Thr Tyr Ile Cys Asn Val Asn His Lys Pro Ser Asn Thr Lys
225                 230                 235                 240

Val Asp Lys Lys Val Glu Pro Lys Ser
                245

<210> SEQ ID NO 70
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
aaacatatga ataccctatt gcctacggc                                      29
```

```
<210> SEQ ID NO 71
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
aaaaagctta ctacgaggag acgg                                              24
```

MELIBIOSE OPERON EXPRESSION SYSTEM

This is a continuation application of U.S. Ser. No. 11/791,988, filed on May 31, 2007, that is a 371 national stage application of International Application PCT Patent Application PCT/EP2005/013012, filed on Dec. 5, 2005, that has benefit of European Patent Application EP 04028920.9, filed on Dec. 7, 2004.

The present invention concerns vectors for the heterologous expression of nucleic acids encoding e.g. polypeptides such as recombinant proteins in prokaryotic hosts. More specifically, the present invention relates to new vectors expressible in a host comprising the promoter region of the melibiose operon operably linked to a transcriptional unit comprising a nucleic acid sequence which is heterologous to said host, whereas the expression of said nucleic acid sequence is controlled by said promoter region of the melibiose operon. The present invention relates further to the use of these vectors for the heterologous expression of nucleic acids encoding e.g. polypeptides.

BACKGROUND OF THE INVENTION

Many systems have been described for the heterologous expression of nucleic acids encoding e.g. polypeptides such as recombinant proteins in prokaryotic systems. However, most heterologous gene expression systems in prokaryotic host systems have relied exclusively on a limited set of bacterial promoters. The most widely used prokaryotic promoters have included the lactose [lac] (Yanisch-Perron et al., 1985, Gene 33, 103-109), and the tryptophan [trp] (Goeddel et al., 1980, Nature (London) 287, 411-416) promoters, and the hybrid promoters derived from these two [tac and trc] (Brosius, 1984, Gene 27: 161-172; Amann and Brosius, 1985, Gene 40, 183-190). Other inducible promoter systems such as the araB promoter inducible by arabinose (WO 86 04356), the Rhamnose promoter rhaSB inducible by L-rhamnose (WO 03068956) or the rhamnose promoter rhaBAD inducible by L-rhamnose (WO 2004/050877) have been described as well for the heterologous expression of proteins. However, many of the known prokaryotic promoters used for heterologous gene expression have drawbacks such as the toxicity of the heterologous product to the host cell, low rates of expression of the product or the formation of non-functional aggregates (inclusion bodies).

There are further inducible promoter systems which have been used in the homologous expression of proteins such as the melibiose operon inducible by melibiose as described by Belyaeva et al., 2000, Mol. Microbiol. 36(1), 211-222. Most of these inducible promoter systems used for homologous expression have the drawback that only low induction rates and therefore low expression of the desired homologous product have been achieved. Furthermore, these promoter systems are not very tightly regulated thus leading to background activity in an uninduced state, which does not allow for strict expression control. For example Belyaeva et al., used different fragments of the melibiose operon fused to a lacZ gene of E. coli for the expression of β-Galactosidase in E. coli. However, the fragments (KK43, JK19) which produced the highest β-Galactosidase activity produced as well the highest background activity.

Thus, there is a need to provide improved prokaryotic expression systems for the heterologous expression of nucleic acid sequences which have not the above-mentioned to disadvantages.

SUMMARY OF THE INVENTION

These and other objects as will be apparent from the foregoing description have been achieved by providing new vectors comprising a prokaryotic promoter region which is useful for high-level expression of a desired heterologous product. Surprisingly, it has been found that the promoter region of the melibiose operon allows for tightly regulated expression of high amounts of heterologous product. In a first aspect, the object of the present invention is to provide a new vector expressible in a host comprising the promoter region of the melibiose operon operably linked to a transcriptional unit comprising a nucleic acid sequence which is heterologous to said host, whereas the expression of said nucleic acid sequence is controlled by said promoter region of the melibiose operon. Also provided are: the use of said new vector for the regulated heterologous expression of a nucleic acid sequence in a prokaryotic host; an isolated and purified nucleic acid sequence expressible in a host comprising the promoter region of the melibiose operon operably linked to a transcriptional unit comprising a nucleic acid sequence which is heterologous to said host, whereas the expression of said nucleic acid sequence is controlled by said promoter region of the melibiose operon; a prokaryotic host transformed with said vector or said isolated and purified nucleic acid sequence; and a method for producing a polypeptide in a host using said vector.

Other objects and advantages will become apparent to those skilled in the art from a review of the ensuing detailed description, which proceeds with reference to the following illustrative drawings, and the attendant claims.

DETAILED DESCRIPTION OF THE INVENTION

Figure 1:
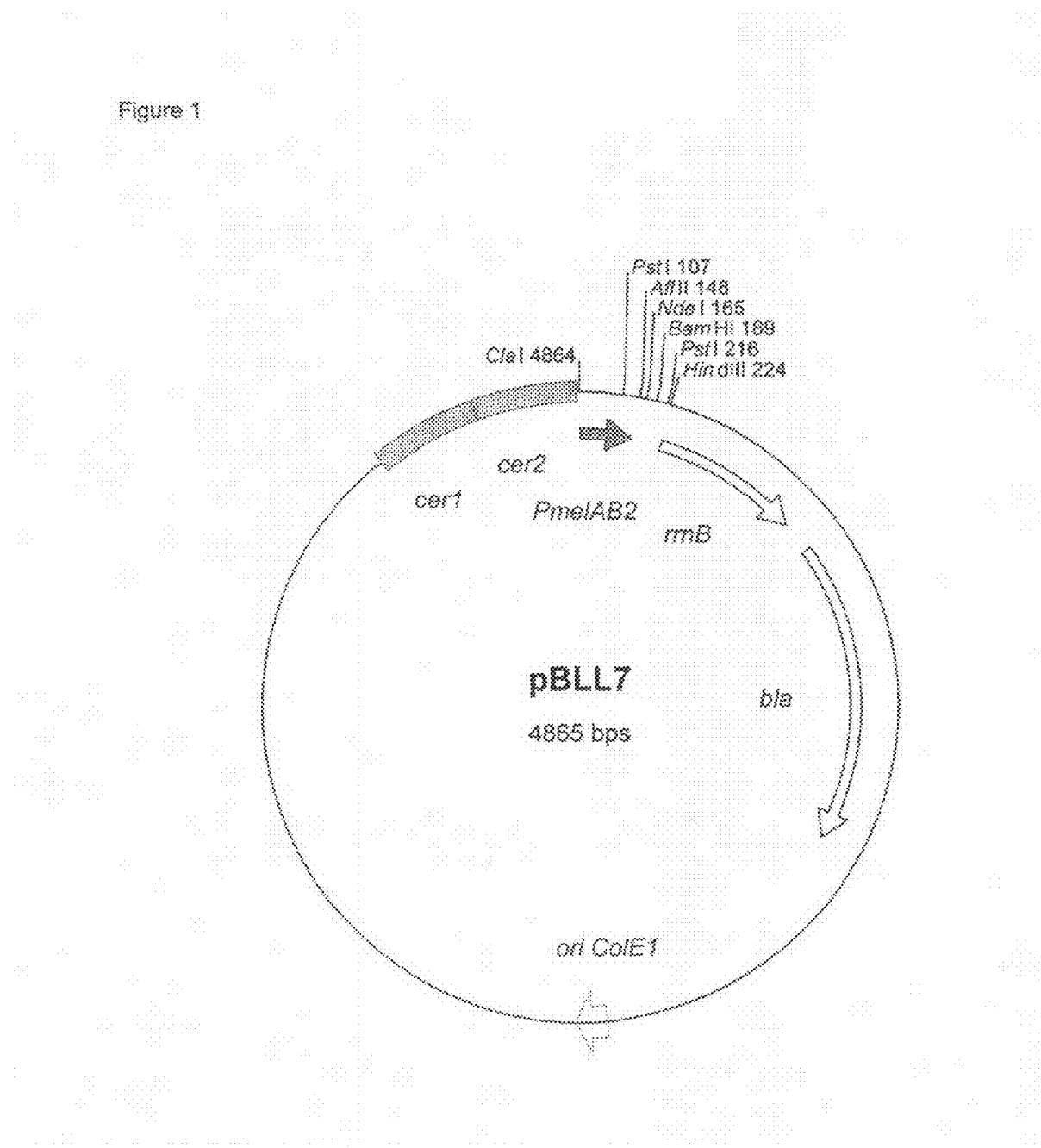
FIG. 1 shows plasmid pBLL7 containing the melibiose inducible melAB2 promoter (PmelAB2) and a transcription termination region (rrnB).

As used herein, the following definitions are supplied in order to facilitate the understanding of the present invention.

A "vector expressible in a host" or "expression vector" is a polynucleic acid construct, generated recombinantly or synthetically, with a series of specified polynucleic acid elements that permit transcription of a particular nucleic acid sequence in a host cell. Typically, this vector includes a transcriptional unit comprising a particular nucleic acid sequence to be transcribed operably linked to a promoter. A vector expressible in a host can be e.g. an autonomously or self-replicating plasmid, a cosmid, a phage, a virus or a retrovirus.

The terms "host", "host cell" and "recombinant host cell" are used interchangeably herein to indicate a prokaryotic cell into which one or more vectors or isolated and purified nucleic acid sequences of the invention have been introduced. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

The term "comprise" is generally used in the sense of include, that is to say permitting the presence of one or more features or components.

"Promoter" as used herein refers to a nucleic acid sequence that regulates expression of a transcriptional unit. A "promoter region" is a regulatory region capable of binding RNA polymerase in a cell and initiating transcription of a downstream (3' direction) coding sequence. Within the promoter region will be found a transcription initiation site (conveniently defined by mapping with nuclease S1), as well as protein binding domains (consensus sequences) responsible for the binding of RNA polymerase such as the putative −35 region and the Pribnow box.

"Melibiose operon" refers to the melibiose operon of E. coli as described in Hanatani et al., 1984, J Biol. Chem, 259(3), 1807-12. The melibiose operon is a positively regulated catabolic operon which contains two divergent promoters. One promoter (melR promoter) is responsible for the expression of the melR gene, that is essential for melibiose-dependent stimulation of the second promoter (melAB promoter). Melibiose-induced transcription from this second promoter initiates cotranscription of the melA gene encoding an alpha-galactosidase and the melB gene encoding a melibiose permease. The melibiose operon contains two Catabolite Regulator Protein binding sites, CRP2 at position −81,5 and CRP1 at position −195,5 upstream of the transcription initiation site of the melAB promoter and five MelR binding sites at positions −42,5 (Site 2'), −62,5 (Site 2), −100,5 (Site1), −120,5 (Site 1') and −238,5 (Site R) upstream of the transcription initiation site of the melAB promoter. With "promoter region of the melibiose operon" is meant the promoter region which regulates expression of the melA gene and the melB gene, including the melAB promoter, the melR promoter, the melR gene and the CRP binding sites and the MelR binding sites. The "melAB promoter" as referred herein consists essentially of the transcription initiation site, the putative −35 region, the Pribnow box, the CRP binding sites and the MelR binding sites. The "melAB promoter deficient in the CRP1 binding site" as referred herein consists essentially of the transcription initiation site, the putative −35 region, the Pribnow box, the CRP2 binding site and the MelR binding sites except Site R. "melAB promoter deficient in the CRP1 binding site" might as well contain a CRP1 binding site which is suppressed or blocked. This can be done by known techniques such as transposon supported mutagenesis or knock-out mutation. Preferably, the "melAB promoter deficient in the CRP1 binding site" does not contain any CRP1 binding site.

Melibiose (6-O-[alpha]-D-galactopyranosyl-D-glucose) is a disaccharide which can be to obtained from raffinose by fermentation with yeast.

"CRP" means "Catabolite Regulator Protein". "CRP" is often referred in the art as "cyclic AMP receptor protein", which has the synonymous meaning. CRP is a regulator protein controlled by cyclic AMP (cAMP) which mediates the activation of catabolic operons such as the melibiose operon.

An "enhancer" is a nucleic acid sequence that acts to potentiate the transcription of a transcriptional unit independent of the identity of the transcriptional unit, the position of the sequence in relation to the transcriptional unit, or the orientation of the sequence. The vectors of the present invention optionally include enhancers.

"Transcriptional unit" as used herein refers to a nucleic acid sequence that is normally transcribed into a single RNA molecule. The transcriptional unit might contain one gene (monocistronic) or two (dicistronic) or more genes (polycistronic) that code for functionally related polypeptide molecules.

A nucleic acid sequence is "operably linked" when it is placed into a functional relationship with another nucleic acid sequence. For example, DNA for a signal sequence is operably linked to DNA for a protein if it is expressed as a preprotein that participates in the secretion of the protein; a promoter is operably linked to a coding sequence if it affects the transcription of the sequence; or a translation initiation region such as a ribosome binding site is operably linked to a nucleic acid sequence encoding e.g. a polypeptide if it is positioned so as to facilitate translation of the polypeptide. Linking can be accomplished by ligation at convenient restriction sites. If such sites do not exist, the synthetic oligonucleotide adaptors or linkers are used in accordance with conventional practice.

"Nucleic acid" or "nucleic acid sequence" or "isolated and purified nucleic acid or nucleic acid sequence" as referred in the present invention might be DNA, RNA, or DNA/RNA hybrid. In case the nucleic acid or the nucleic acid sequence is located on a vector it is usually DNA. DNA which is referred to herein can be any polydeoxynucleotide sequence, including, e.g. double-stranded DNA, single-stranded DNA, double-stranded DNA wherein one or both strands are composed of two or more fragments, double-stranded DNA wherein one or both strands have an uninterrupted phosphodiester backbone, DNA containing one or more single-stranded portion(s) and one or more double-stranded portion(s), double-stranded DNA wherein the DNA strands are fully complementary, double-stranded DNA wherein the DNA strands are only partially complementary, circular DNA, covalently-closed DNA, linear DNA, covalently cross-linked DNA, cDNA, chemically-synthesized DNA, semi-synthetic DNA, biosynthetic DNA, naturally-isolated DNA, enzyme-digested DNA, sheared DNA, labeled DNA, such as radiolabeled DNA and fluorochrome-labeled DNA, DNA containing one or more non-naturally occurring species of nucleic acid. DNA sequences can be synthesized by standard chemical techniques, for example, the phosphotriester method or via automated synthesis methods and PCR methods. The purified and isolated DNA sequence may also be produced by enzymatic techniques.

RNA which is referred to herein can be e.g. single-stranded RNA, cRNA, double-stranded RNA, double-stranded RNA wherein one or both strands are composed of two or more fragments, double-stranded RNA wherein one or both strands have an uninterrupted phosphodiester backbone, RNA containing one or more single-stranded portion(s) and one or more double-stranded portion(s), double-stranded RNA wherein the RNA strands are fully complementary, double-stranded RNA wherein the RNA strands are only partially complementary, covalently crosslinked RNA, enzyme-digested RNA, sheared RNA, mRNA, chemically-synthesized RNA, semi-synthetic RNA, biosynthetic RNA, naturally-isolated RNA, labeled RNA, such as radiolabeled RNA and fluorochrome-labeled RNA, RNA containing one or more non-naturally-occurring species of nucleic acid.

With "variants" or "variants of a sequence" is meant a nucleic acid sequence that varies from the reference sequence by conservative nucleic acid substitutions, whereby one or more nucleic acids are substituted by another with same characteristics. Variants encompass as well degenerated sequences, sequences with deletions and insertions, as long as such modified sequences exhibit the same function (functionally equivalent) as the reference sequence.

As used herein, the terms "polypeptide", "peptide", "protein", "polypeptidic" and "peptidic" are used interchangeably to designate a series of amino acid residues connected to the other by peptide bonds between the alpha-amino and carboxy groups of adjacent residues.

The term "isolated and purified nucleic acid sequence" refers to the state in which the nucleic acid sequence will be, in accordance with the present invention. The nucleic acid sequence will be free or substantially free of material with which they are naturally associated such as other nucleic acids with which they are found in their natural environment, or the environment in which they are prepared (e.g. cell culture) when such preparation is by recombinant technology practised in vitro or in vivo.

The terms "transformation", "transformed" or "introducing a nucleic acid into a host cell" denote any process wherein an extracellular nucleic acid like a vector, with or without accompanying material, enters a host cell. The term "cell transformed" or "transformed cell" means the cell or its progeny into which the extracellular nucleic acid has been introduced and thus harbours the extracellular nucleic acid. The nucleic acid might be introduced into the cell so that the nucleic acid is replicable either as a chromosomal integrant or as an extra chromosomal element. Transformation of appropriate host cells with e.g. an expression vector can be accomplished by well known methods such as microinjection, electroporation, particle bombardement or by chemical methods such as Calcium phosphate-mediated transformation, described e.g. in Maniatis et al. 1982, Molecular Cloning, A laboratory Manual, Cold Spring Harbor Laboratory or in Ausubel et al. 1994, Current protocols in molecular biology, John Wiley and Sons.

"Heterologous nucleic acid sequence" or "nucleic acid sequence heterologous to a host" means a nucleic acid sequence which encodes e.g. an expression product such as a polypeptide that is foreign to the host ("heterologous expression" or "heterologous product") i.e. a nucleic acid sequence originating from a donor different from the host or a chemically synthesized nucleic acid sequence which encodes e.g. an expression product such as a polypeptide that is foreign to the host. In case the host is a particular prokaryotic species, the heterologous nucleic acid sequence is preferably originated from a different genus or family, more preferred from a different order or class, in particular from a different phylum (division) and most particular from a different domain (empire) of organisms.

The heterologous nucleic acid sequence originating from a donor different from the host can be modified, before it is introduced into a host cell, by mutations, insertions, deletions or substitutions of single nucleic acids or a part of the heterologous nucleic acid sequence as long as such modified sequences exhibit the same function (functionally equivalent) as the reference sequence. A heterologous nucleic acid sequence as referred herein encompasses as well nucleic sequences originating from a different domain (empire) of organisms such as from eukaryotes (of eukaryotic origin) such as e.g. human antibodies which have been used in phage display libraries and of which single nucleic acids or a part of the nucleic acid sequences have been modified according to the "codon usage" of a prokaryotic host.

"Signal sequence" or "signal peptide sequence" refers to a nucleic acid sequence which encodes a short amino acid sequence (i.e., signal peptide) present at the NH2-terminus of certain proteins that are normally exported by cells to non-cytoplasmic locations (e.g., secretion) or to be membrane components. Signal peptides direct the transport of proteins from the cytoplasm to non-cytoplasmic locations.

"Translation initiation region" is a signal region which promotes translation initiation and which functions as the ribosome binding site such as the Shine Dalgarno sequence.

"Transcription termination region" refers to a sequence which causes RNA polymerase to terminate transcription. The transcription termination region is usually part of a transcriptional unit and increases the stability of the mRNA.

"Antibody" refers to a class of plasma proteins produced by the B-cells of the immune system after stimulation by an antigen. Mammal (i.e. Human) antibodies are immunoglobulins of the Ig G, M, A, E or D class. The term "antibody" as used for the purposes of this invention includes, but is not limited to, polyclonal antibodies, monoclonal antibodies, anti-idiotypic antibodies and auto-antibodies present in autoimmune diseases, such as diabetes, multiple sclerosis and rheumatoid arthritis as well as chimeric antibodies. The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 more amino acids.

The term antibody is used to mean whole antibodies and binding fragments thereof. Binding fragments include single chain fragments, Fv fragments and Fab fragments. The term Fab fragment is sometimes used in the art to mean the binding fragment resulting from papain cleavage of an intact antibody. The terms Fab' and F(ab')2 are sometimes used in the art to refer to binding fragments of intact antibodies generated by pepsin cleavage. In the context of the present invention, Fab is used to refer generically to double chain binding fragments of intact antibodies having at least substantially complete light and heavy chain variable domains sufficient for antigen-specific bindings, and parts of the light and heavy chain constant regions sufficient to maintain association of the light and heavy chains. An example of such Fab is described in Skerra et al., 1988, Science 240 (4855), 1038-41, for instance. A Fab fragment e.g. of the IgG idiotype might or might not contain at least one of the two cysteine residues that form the two inter-chain disulfide bonds between the two heavy chains in the intact immunoglobulin. Usually, Fab fragments are formed by complexing a full-length or substantially full-length light chain with a heavy chain comprising the variable domain and at least the CH1 domain of the constant region.

In addition, the C-terminal cysteine on the light chain may be replaced with serine or another amino acid to eliminate the interchain disulfide bond between the heavy and light chains according to the present invention. Further encompassed are chimeric antibodies which are antibodies whose light and heavy chain genes have been constructed, typically by genetic engineering, from immunoglobulin gene segments (e.g., segments encoding the variable region and segments encoding the constant region), for example, belonging to different species. For example, the variable (V) segments of the genes from a mouse monoclonal antibody can be joined to human constant (C) segments, such as IgG1 an IgG4. A typical chimeric antibody is thus a hybrid protein consisting of the V or antigen-binding domain from a mouse antibody and a C or effector domain from a human antibody. Chimeric antibodies have the same or similar binding specificity and affinity as a mouse or other nonhuman antibody that provides the variable regions of the antibody.

The term "human antibody" includes antibodies having variable and constant regions (if present) derived from human germline immunoglobulin sequences including either natural or artifical, engineered affinity maturation. Human antibodies of the invention can include amino acid residues not encoded by human germline immunoglobulin sequences (e.g. mutations introduced by random or site-specific mutagenesis in vitro or by somatic mutation in vivo). However, the term "human antibody" does include antibodies in which CDR sequences derived from the germline of another mammalian species, such as a mouse, have been grafted onto human framework sequences (i.e. humanized antibodies). Functional variants of such "human antibodies", e.g. truncated versions thereof or engineered muteins where e.g. individual proline or cysteine residues have been engineered by the means of genetic engineering well known in the art are encompassed by the term, in contrast. Examples of such may be found e.g. in WO 98/02462. However, the term only relates to the amino acid sequence of such antibody, irrespective of any glycosylation or other chemical modification of the peptide backbone.

In one aspect, the present invention provides a vector expressible in a host comprising the promoter region of the melibiose operon operably linked to a transcriptional unit comprising a nucleic acid sequence which is heterologous to said host, whereas the expression of said nucleic acid sequence is controlled by said promoter region of the melibiose operon.

The vector according to the invention is preferably an autonomously or self-replicating plasmid, a cosmid, a phage, a virus or a retrovirus. A wide variety of host/vector combinations may be employed in expressing the nucleic acid sequences of this invention. Useful expression vectors, for example, may consist of segments of chromosomal, non-chromosomal and/or synthetic nucleic acid sequences. Suitable vectors include vectors with specific host range such as vectors specific for e.g. $E.$ $coli$ as well as vectors with broad-host-range such as vectors useful for Gram-negative bacteria. "Low-copy", "medium-copy" as well as "high copy" plasmids can be used.

Useful vectors for e.g. expression in $E.$ $coli$ are: pQE70, pQE60 and pQE-9 (QIAGEN, Inc.); pBluescript Vektoren, Phagescript Vektoren, pNH8A, pNH16a, pNH18A, pNH46A (Stratagene Cloning Systems, Inc.); ptrc99a, pKK223-3, pKK233-3, pDR540, pRIT5 (Pharmacia Bio-tech, Inc.); pLG338, pACYC184, pBR322, pUC18, pUC19, pKC30, pRep4, pACYC177, pACYC184, pRSF1010 and pBW22 [Wilms et al., 2001, Biotechnology and Bioengineering, 73 (2) 95-103] or derivates thereof such as plasmid pBLL15 or plasmid pAKL15E. Further useful plasmids are well known to the person skilled in the art and are described e.g. in "Cloning Vectors" (Eds. Pouwels P. H. et al. Elsevier, Amsterdam-New York-Oxford, 1985).

Preferred vectors of the present inventions are autonomously or self-replicating plasmids, more preferred are vectors with specific host range such as vectors specific for e.g. $E.$ $coli$. Most preferred are pBR322, pUC18, pACYC177, pACYC184, pRSF1010 and pBW22 or derivates thereof such as plasmid pBLL15 or plasmid pAKL15E, particularly preferred is pBW22 or derivates thereof such as plasmid pBLL15 or plasmid pAKL15E, more particularly preferred are pBLL15 or pAKL15E, most particularly preferred is pAKL15E.

In a preferred embodiment, the promoter region of the melibiose operon used in the present invention is the melAB promoter. According to a more preferred embodiment of the invention, the melAB promoter is deficient in the CRP1 binding site. In a particular preferred embodiment, the melAB promoter deficient in the CRP1 binding site consists of the sequence SEQ ID NO. 1, a sequence complementary thereof and variants thereof. Usually, the MelR binding sites of the promoter region have not been modified.

The promoter region of the melibiose operon, the melAB promoter, the melAB promoter deficient in the CRP1 binding site, as well as the melAB promoter deficient in the CRP1 binding site consisting of the sequence SEQ ID NO. 1, a sequence complementary thereof and variants thereof, used in the present invention are usually from the melibiose operon of $E.$ $coli$ or from a functional equivalent promoter region of other prokaryotic organisms, in particular of organisms of the family of enterobacteriaceae. Preferably, the promoter region of the melibiose operon, the melAB promoter, the melAB promoter deficient in the CRP1 binding site, as well as the melAB promoter deficient in the CRP1 binding site consisting of the sequence SEQ ID NO. 1, a sequence complementary thereof and variants thereof, are from the melibiose operon of $E.$ $coli$. A functional equivalent promoter region of other prokaryotic organisms encompasses a promoter region which is inducible by melibiose i.e. a promoter region having a higher expression activity in the presence than in the absence of melibiose.

The transcriptional unit according to the present invention usually further comprises a translation initiation region upstream of the initiation point of the translation of said transcriptional unit, said translation initiation region consisting of the sequence AGGAGATATACAT (SEQ ID NO. 2), whereas the translation initiation region is operably linked to the nucleic acid sequence. The sequence AGGAGATATACAT (SEQ ID NO. 2) is usually located upstream directly adjacent to the initiation point of the translation of the transcriptional unit which can be ATG, GTG or TTG.

Usually, said transcriptional unit further comprises a signal sequence operably linked to the heterologous nucleic acid sequence of the invention. In case a dicistronic or polycistronic transcriptional unit is used, different or identical signal sequences operably linked to each of the cistrons can be applied. Preferably different signal sequences are used in such a case. The signal sequence used can be a prokaryotic or a eukaryotic signal sequence. Usually, prokaryotic signal sequences are applied. Eukaryotic signal sequences which can be used and which are particular useful for *E. coli* are e.g. human ceruloplasmin signal sequence, human neutrophil defensin 1,2,3 precursor signal sequence or the signal peptide of *Chlamydomonas reinhardtii* arylsulfatase as described in WO 03068956. Prokaryotic signal sequences usually applied are signal peptides of periplasmatic binding proteins for sugars, amino acids, vitamins and ions, such as e.g. PelB (*Erwinia chrysantemi*, pectate lyase precursor), PelB (*Erwinia carotovora*, pectate lyase precursor), PelB (*Xanthomonas campestris*, pectate lyase precursor), LamB (*E. coli*, maltoporin precursor), MalE (*E. coli*, maltose-binding protein precursor), Bla (*E. coli*, beta-lactamase), OppA (*E. coli*, periplasmic oligopeptide-binding protein), TreA (*E. coli*, periplasmic trehalase precursor), MppA (*E. coli*, periplasmic murein peptide-binding protein precursor), BglX (*E. coli*, periplasmic beta-glucosidase precursor), ArgT (*E. coli*, lysine-arginine-ornithine binding periplasmic protein precursor), MalS (*E. coli*, α-amylase precursor), HisJ (*E. coli*, histidine-binding periplasmic protein precursor), XylF (*E. coli*, D-xylose-binding periplasmic protein precursor), FecB (*E. coli*, dicitrate-binding periplasmic protein precursor), OmpA (*E. coli*, outer membrane protein A precursor) and PhoA (*E. coli*, alkaline phosphatase precursor).

In a preferred embodiment, the signal sequence is selected from the *E. coli* signal peptides LamB (Maltoporin precursor), MalE (Maltose-binding protein precursor), Bla (Beta-lactamase), OppA (Periplasmic oligopeptide-binding protein), TreA (Periplasmic trehalase precursor), MppA (Periplasmic murein peptide-binding protein precursor), BglX (Periplasmic beta-glucosidase precursor), ArgT (Lysine-arginine-ornithine binding periplasmic protein precursor), MalS (α-amylase precursor), HisJ (Histidine-binding periplasmic protein precursor), XylF (D-Xylose-binding periplasmic protein precursor), FecB (Dicitrate-binding periplasmic protein precursor), OmpA (Outer membrane protein A precursor) and PhoA (Alkaline phosphatase precursor). These are particularly useful for heterologous expression in *E. coli*. More preferred are the *E. coli* signal peptides LamB (Maltoporin precursor), MalE (Maltose-binding protein precursor), Bla (Beta-lactamase), TreA (periplasmic trehalase precursor), ArgT (Lysine-arginine-ornithine binding periplasmic protein precursor), FecB (Dicitrate-binding periplasmic protein precursor). Most particular preferred are the *E. coli* signal peptides LamB (Maltoporin precursor) and MalE (Maltose-binding protein precursor).

The signal sequences to be employed in the expression vectors of the present invention can be obtained commercially or synthesized chemically. For example, signal sequences can be synthesized according to the solid phase phosphoramidite triester method described, e.g., in Beaucage & Caruthers, Tetrahedron Letts. 22:1859-1862 (1981), using an automated synthesizer, as described in Van Devanter et. al., Nucleic Acids Res. 12:6159-6168 (1984). Purification of oligonucleotides can be performed by either native acrylamide gel electrophoresis or by anion-exchange HPLC as described in Pearson & Render, J. Chrom. 255:137-149 (1983).

Usually, said transcriptional unit further comprises a transcription termination region selected from rrnB, RNA 1, T7Te, rrnB T1, trp a L126, trp a, tR2, T3Te, P14, tonB t, and trp a L153. Preferably, the rrnB transcriptional terminator sequence is used.

The heterologous nucleic acid sequence according to the present invention encodes an expression product that is foreign to the host. In case the host is a prokaryotic species such as *E. coli* the nucleic acid sequence of interest is more preferably from another class like the gammaproteobacteria such as from e.g. *Burkholderia* sp., in particular from a different phylum such as archae bacteria, and most particular from an eukaryotic organism such as mammals in particular from humans. However, the heterologous nucleic acid sequence might be modified according to the "codon usage" of the host. The heterologous sequence according to the present invention is usually a gene of interest. The gene of interest preferably encodes a heterologous polypeptide such as a structural, regulatory or therapeutic protein, or N- or C-terminal fusions of structural, regulatory or therapeutic protein with other proteins ("Tags") such as green fluorescent protein or other fusion proteins. The heterologous nucleic acid sequence might encode as well a transcript which can be used in the form of RNA, such as e.g. antisense-RNA.

The protein may be produced as an insoluble aggregate or as a soluble protein which is present in the cytoplasm or in the periplasmic space of the host cell, and/or in the extracellular medium. Preferably, the protein is produced as a soluble protein which is present in the periplasmic space of the host cell and/or in the extracellular medium. Examples of proteins include hormones such as growth hormone, growth factors such as epidermal growth factor, analgesic substances like enkephalin, enzymes like chymotrypsin, antibodies, receptors to hormones and includes as well proteins usually used as a visualizing marker e.g. green fluorescent protein.

Other proteins of interest are growth factor receptors (e.g., FGFR, PDGFR, EFG, NGFR, and VEGF) and their ligands. Other proteins are G-protein receptors and include substance K receptor, the angiotensin receptor, the [alpha]- and [beta]-adrenergic receptors, the serotonin receptors, and PAF receptor (see, e.g. Gilman, Ann. Rev. Biochem. 56, 625-649 (1987). Other proteins include ion channels (e.g., calcium, sodium, potassium channels), muscarinic receptors, acetylcholine receptors, GABA receptors, glutamate receptors, and dopamine receptors (see Harpold, U.S. Pat. Nos. 5,401,629 and 5,436,128). Other proteins of interest are adhesion proteins such as integrins, selecting, and immunoglobulin superfamily members (see Springer, Nature 346, 425-433 (1990). Osborn, Cell 62, 3 (1990); Hynes, Cell 69, 11 (1992)). Other proteins are cytokines, such as interleukins IL-1 through IL-13, tumor necrosis factors [alpha] and [beta], interferons [alpha], [beta], and [gamma], tumor growth factor Beta (TGF-[beta]), colony stimulating factor (CSF) and granulocyte monocyte colony stimulating factor (GM-CSF) (see Human Cytokines: Handbook for Basic & Clinical Research. Aggrawal et al. eds., Blackwell Scientific, Boston, Mass. 1991). Other proteins of interest are intracellular and intercellular messengers, such as, adenyl cyclase, guanyl cyclase, and phospholipase C. Drugs are also proteins of interest. The heterologous protein of interest can be of human, mammalian or prokaryotic origin. Other proteins are antigens, such as glycoproteins and carbohydrates from microbial pathogens, both viral and bacterial, and from tumors.

Other proteins are enzymes like chymosin, proteases, polymerases, dehydrogenases, nucleases, glucanases, oxidases, α-amylase, oxidoreductases, lipases, amidases nitril hydratases, esterases or nitrilases.

Preferably, the heterologous nucleic acid sequence, according to the present invention, encodes a polypeptide, more preferably an antibody and most preferably a Fab fragment. In particular a human antibody or a humanised antibody, more particularly a human Fab fragment is encoded by the nucleic acid sequence. The human Fab fragment encoded by the nucleic acid sequence is preferably either a human antibody fragment or a human antibody fragment that was grafted with at least one CDR from another mammalian species. In one more preferred embodiment, the human Fab fragment is a fully human HuCAL-Fab as obtainable from an artificial, consensus-framework-based human antibody phage library that was artifically randomized in the CDR as described by Knappik et al., 2000, J. Mol. Biol. 296 (1), 57-86.

In another more preferred optional embodiment, the, optionally chimeric, CDR grafted, human Fab fragment is a non-HuCAL-Fab as opposed to the HuCAL Fab definition in the foregoing, which in case of a fully human Fab fragment preferably means that it does not share the HuCAL consensus sequence framework but its non-CDR sequence portions are at least 70% more preferably 85%, most preferably 95% identical in amino acid sequence to the respective variable and constant light and heavy chains germline-encoded sequences, additionally and more preferably that its CDRs are directly obtained from naturally occurring genomic sequences of lymphoid cells including genomic affinity maturation events.

The Fab fragment is preferably derived from an IgG antibody and does not contain cysteine residues that form the two interchain disulfide bonds between the two heavy chains in the intact immunoglobulin. In particular, the heavy and the light chain of the antibody or preferably of the Fab fragment are encoded by a dicistronic transcriptional unit, whereas each chain is operably linked to a signal sequence and an identical translation initiation region upstream of the initiation point of the translation of the transcriptional unit. Preferably, the translation initiation region consists of the sequence AGGAGATATACAT (SEQ ID NO. 2).

In the present invention, the order and the distance in which the signal sequence and the heterologous nucleic acid sequence are arranged within the expression vectors can be varied. In preferred embodiments, the signal sequence is 5' (upstream) to the nucleic acid sequence encoding e.g. the polypeptide of interest. The signal peptide sequence and the nucleic acid sequence encoding e.g. the polypeptide of interest can be separated by zero to about 1000 amino acids. In preferred embodiments, the signal peptide sequence and nucleic acid sequence encoding e.g. the polypeptide of interest are directly adjacent to each other, i.e. separated by zero nucleic acids.

Preferably, the promoter region and the operably linked transcriptional unit of the vector of the present invention consist of the sequence SEQ ID NO. 3, a sequence complementary thereof and variants thereof.

More preferably, the promoter region and the operably linked transcriptional unit of the vector of the present invention consists of the sequence SEQ ID NO. 4, a sequence complementary thereof and variants thereof.

Also encompassed by the present invention is the use of a vector according to the invention for the regulated heterologous expression of a nucleic acid sequence in a prokaryotic host. The expression can be regulated by the amount of melibiose available to the prokaryotic host. Usually, the amount of melibiose in the medium of the cultured prokaryotic host is between 0.01 and 100 g/l, preferably between 0.1 and 10 g/l, more preferably between 1 and 5 g/l.

Preferably, the heterologous nucleic acid sequence encodes for a polypeptide, more preferably for an antibody and most preferably for a Fab fragment, whereas the heavy and light chains of the antibody or the Fab fragment are expressed in equal amounts, thus leading to high concentrations of functional antibody or Fab fragment. In particular a human antibody or a humanised antibody, more particular a human Fab fragment, most particular a human Fab fragment as described above is encoded by the heterologous nucleic acid sequence.

In order to obtain high concentrations of functional antibody or Fab fragment it is essential to have an equal amount of the heavy and light chains being expressed. In case one of both chains is overproduced compared to the other chain, non-reducible high molecular weight immunoreactive aggregates can be built, which is undesirably. It has been surprisingly found that with the vectors of the present invention high titers of functional antibodies can be obtained whereas only very low amounts of overproduced light or heavy chain or high molecular weight immunoreactive aggregates are built. Usually, less than 20%, preferably less than 10% of the expressed amount of antibody or Fab fragment are expressed as overproduced light or heavy chain or high molecular weight immunoreactive aggregates. The amount of the heavy and light chains overproduced and of high molecular weight immunoreactive aggregates can be measured by analysing extracts of the host expressing the antibody or the Fab fragment such as lysozyme extracts of the cultured host cell using SDS-PAGE or Western blot.

In still another aspect, the invention provides an isolated and purified nucleic acid sequence expressible in a host comprising the promoter region of the melibiose operon operably linked to a transcriptional unit comprising a nucleic acid sequence which is heterologous to said host, whereas the expression of said nucleic acid sequence is controlled by said promoter region of the melibiose operon. The melAB promoter is the preferred promoter region. More preferred is the melAB promoter deficient in the CRP1 binding site. Most preferred, the isolated and purified nucleic acid sequence consists of SEQ ID NO. 1, a sequence complementary thereof and variants thereof, in particular the isolated and purified nucleic acid sequence consists of SEQ ID NO. 3, a sequence complementary thereof and variants thereof, most particular the isolated and purified nucleic acid sequence consists of SEQ ID NO. 4, a sequence complementary thereof and variants thereof. The isolated and purified nucleic acid sequence of this invention can be isolated according to standard PCR protocols and methods well known in the art. Said purified and isolated DNA sequence can further comprise one or more regulatory sequences, as known in the art e.g. an enhancer, usually employed for the expression of the product encoded by the nucleic acid sequence.

In order to select host cells successfully and stably transformed with the vector or the isolated and purified nucleic acid sequence of the present invention, a gene that encodes a selectable marker (e.g., resistance to antibiotics) can be introduced into the host cells along with the nucleic acid sequence of interest. The gene that encodes a selectable marker might be located on the vector or on the isolated and purified nucleic acid sequence or might optionally be co-introduced in separate form e.g. on a separate vector. Various selectable markers can be used including those that confer resistance to antibiotics, such as hygromycin, ampicillin and tetracyclin. The amount of the antibiotic can be adapted as desired in order to create selective conditions. Usually, one selectable markers is used. As well reporter genes such as fluorescent proteins can be introduced into the host cells along with the nucleic acid sequence of interest, in order to determine the efficiency of transformation.

Another aspect of the present invention is to provide a prokaryotic host transformed with a vector of the present invention. In a particular embodiment of the invention the prokaryotic host is transformed with plasmid pBLL15 or plasmid pAKL15E, preferably with plasmid pAKL15E comprising two different coding region in its dicistronic expression cassette for expressing a secreted, heterodimeric protein in such host cell such as e.g. a Fab. Preferably, such heterodimeric protein is a Fab. In another embodiment of the invention the prokaryotic host is transformed with an isolated and purified nucleic acid sequence of the present invention.

A wide variety of prokaryotic host cells are useful in expressing the heterologous nucleic acid sequences of this invention. These hosts may include strains of Gram-negative cells such as *E. coli* and *Pseudomonas*, or Gram postitive cells such as *Bacillus* and *Streptomyces*. Preferably, the host cell is a Gram-negative cell, more preferably an *E. coli* cell. *E. coli* which can be used are e.g. the strains TG1, W3110, DH1, XL1-Blue and Origami, which are commercially available or can be obtained via the DSMZ (Deutsche Sammlung von Mikroorganismen and Zellkulturen GmbH, Braunschweig, Germany). Most preferably, W3110 is used. The host cell might or might not metabolise Melibiose. A host cell which is ordinarily capable to uptake and metabolise melibiose like *E. coli* might be modified to be deficient in one or more functions related to the uptake and/or metabolism of melibiose. Deficiency in one or more functions related to the uptake and/or metabolism of melibiose can be achieved by e.g. suppressing or blocking the expression of a gene coding for a protein related to the uptake and/or metabolism of melibiose such as the melA gene coding for alpha-galactosidase. This can be done by known techniques such as transposon supported mutagenesis or knock-out mutation. Usually, the prokaryotic host corresponds to the signal sequences chosen, e.g. in case signal sequences of *E. coli* are used, the host cell is usually a member of the same family of the enterobacteriaceae, more preferably the host cell is an *E. coli* strain.

Further provided with the present invention is a method for producing a polypeptide in a host cell, comprising the steps of
a) constructing a vector,
b) transforming a prokaryotic host with said vector,
c) allowing expression of said polypetide in a cell culture system under suitable conditions,
d) recovering said polypeptide from the cell culture system.

The vector used, as well as its construction and the transformation of a prokaryotic host are as defined above, whereas the heterologous nucleic acid sequence comprised by the vector encodes a polypeptide. Preferably, the polypeptide produced is an antibody and most preferably a Fab fragment, whereas the heavy and light chains of the antibody or the Fab fragment are expressed in the cell culture system in equal amounts, thus leading to high concentrations of functional antibody or Fab fragment.

As cell culture system continuous or discontinous culture such as batch culture or fed batch culture can be applied in culture tubes, shake flasks or bacterial fermentors. Host cells are usually cultured in conventional media as known in the art such as complex media like "nutrient yeast broth medium" or a glycerol containing medium as described by Kortz et al., 1995, J. Biotechnol. 39, 59-65 or a mineral salt media as described by Kulla et al., 1983, Arch. Microbiol, 135, 1. The preferred medium for carrying out the expression of said polypeptide is a glycerol containing medium, more preferably the medium described by Kortz et al., 1995, J. Biotechnol. 39, 59-65.

The medium might be modified as appropriate e.g. by adding further ingredients such as buffers, salts, vitamins or amino acids. As well different media or combinations of media can be used during the culturing of the cells. Preferably, the medium used as basic medium should not include melibiose, in order to achieve a tight regulation of the melibiose promoter region. Melibiose is usually added after the culture has reached an appropriate $OD_{600}$ depending on the culture system. Usually, the amount of melibiose in the medium of the cultured prokaryotic host is between 0.01 and 100 g/l, preferably between 0.1 and 10 g/l, more preferably 1 and 5 g/l. For batch culture the usual $OD_{600}$ is usually 0.4 or higher. Appropriate pH ranges are e.g. 6-8 preferably 7-7.5, appropriate culture temperatures are between 10 and 40, preferably between 20 and 37° C. The cells are incubated usually as long as it takes until the maximum amount of expressed product has accumulated, preferably between 1 hour and 20 days, more preferably between 5 hours and 3 days. The amount of expressed product depends on the culture system used. In shake flask culture usually expressed product in the amount of 0.5 g/l culture medium can be produced with a host transformed with the vector of the present invention. Using a fermentor culture in a batch and/or fed-batch mode expressed product in the amount of usually more than 0.5 g/l fermentation broth, preferably more than 1 g/l, more preferably more than 1.3 g/l can be obtained.

Following expression in the host cell, the expressed product such as the polypeptide of interest can then be recovered from the culture of host cells. When the polypeptide of interest are immunoglobulin chains, the heavy chain and the light chain are normally each expressed in the host cell and secreted to the periplasm of the cell. The signal peptides encoded by the signal sequences in the expression vector are then processed from the immunoglobulin chains. The mature heavy and light chains are then assembled to form an intact antibody or a Fab fragment. In order to obtain a maximum yield of the expressed product the cells are usually harvested at the end of the culture and lysed, such as lysing by lysozyme treatment, sonication or French Press. Thus, the polypeptides are usually first obtained as crude lysate of the host cells. They can then be purified by standard protein purification procedures known in the art which may include differential precipitation, molecular sieve chromatography, ion-exchange chromatography, isoelectric focusing, gel electrophoresis, affinity, and immunoaffinity chromatography. These well known and routinely practiced methods are described in, e.g., Ausubel et al., supra., and Wu et al. (eds.), Academic Press Inc., N.Y.; Immunochemical Methods In Cell And Molecular Biology. For example, for purification of recombinantly produced immunoglobulins or Fab fragments, they can be purified with immunoaffinity chromatography by passage through a column containing a resin which has bound thereto target molecules to which the expressed immunoglobulins can specifically bind.

The present invention also relates to methods and means for the intracellular heterologous expression of nucleic acids encoding e.g. polypeptides in a prokaryotic host. In particular the present invention relates to vectors for the intracellular expression of a heterologous polypeptide in a prokaryotic host, whereby the vector is expressible in a prokaryotic host comprising the promoter region of the melibiose operon operably linked to a transcriptional unit comprising a nucleic acid sequence which is heterologous to said host. Since in this embodiment of the vector of the present invention the nucleic acid sequence is not linked to a prokaryotic signal sequence upon transforming a prokaryotic host cell with the vector and expression of the polypeptide encoded by the heterologous nucleic acid the polypeptide will not be transported from the cytoplasm to non-cytoplasmic locations. Instead the polypeptide will be expressed within the cytoplasm in form of inclusion bodies or insoluble form. Thus upon expression the polypeptide can be isolated and purified by well-known procedures from the cell, in particular from cell extract. The present invention also provides for the use of said vectors for the regulated intracellular expression of a heterologous nucleic acid sequence in a prokaryotic host cell; a prokaryotic host or prokaryotic host cell transformed with said vector; a method for the intracellular production of a heterologous polypeptide in a prokaryotic host using said vector; and a vector for the intracellular production of a heterologous polypeptide comprising a promoter region, a heterologous nucleic acid sequence encoding a heterologous polypeptide and a translation initiation region consisting of the sequence AGGAGATATACAT (SEQ ID NO: 2).

In a preferred embodiment of the vector which can be used for the intracellular expression the promoter region of the melibiose operon is the melAB promoter which preferably is deficient in the CRP1 binding site. Particularly preferred the melAB promoter deficient in the CRP1 binding site consists of the sequence depicted in SEQ ID No. 1, a sequence complementary thereof and a variant sequence thereof. In another preferred embodiment of the invention the transcriptional unit of the vector further comprises a translation initiation region upstream of the initiation point of the translation of said transcriptional unit, whereby the translation initiation region consists of the sequence AGGAGATATACAT (SEQ ID No. 2). In further preferred embodiments the vector to be used for the intracellular expression comprises a transcription termination region such as the rrnB transcriptional terminator sequence. According to the invention the heterologous nucleic acid sequence may encode a polypeptide such as an antibody, an antibody fragment etc.

Those skilled in the art will appreciate that the invention described herein is susceptible to variations and modifications other than those specifically described. It is to be understood that the invention includes all such variations and modifications without departing from the spirit or essential characteristics thereof. The invention also includes all of the steps, features, compositions and compounds referred to or indicated in this specification, individually or collectively, and any and all combinations or any two or more of said steps or features. The present disclosure is therefore to be considered as in all aspects illustrated and not restrictive, the scope of the invention being indicated by the appended Claims, and all changes which come within the meaning and range of equivalency are intended to be embraced therein. Various references are cited throughout this Specification, each of which is incorporated herein by reference in its entirety.

The foregoing description will be more fully understood with reference to the following Examples. Such Examples, are, however, exemplary of methods of practising the present invention and are not intended to limit the scope of the invention.

EXAMPLES

Example 1

The *Escherichia coli* W3110 genome was scanned for positively regulated operons. Based on the genomic data which are available on the KEGG database (Kyoto Encyclopedia of Genes and Genomes, http://www.genome.ad.jp/kegg/kegg2.html) positively regulated catabolic promoters were identified and analysed for their use in expression plasmids. The promoters should be tightly regulated and induced by a cheap and non-toxic and therefore industrially useful compound. The following promoters of different positively regulated catabolic operons were chosen Construction of Expression Plasmids with Positively Regulated Promoters pip promoter (propionate inducible)
    gutA promoter (glucitol inducible)
    melAB2 promoter (melibiose inducible)

The precise DNA fragments which contain the promoter elements were selected based on the available information on the corresponding regulator binding sites. Chromosomal DNA of *Escherichia coli* was isolated by the method of Pitcher et al., 1989, Letters in Applied Microbiology 8, 151-156. The promoter fragments were amplified from the chromosomal DNA of strain W3110 by PCR using the following primers. The restriction sites of ClaI and AflII are underlined. The sequences of the fragments are as follows:

```
Pprp    Pprp-5    5' aaa atc gat aaa tga aac gca tat ttg 3'
                  (SEQ ID NO: 5)
        Pprp-3    5' aaa ctt aag ttg tta tca act tgt tat 3'
                  (SEQ ID NO: 6)
AAAATCGATAACTGAAACGCATATTTGCGGATTAGTTCATGACTTTATCTCTAACAAA
TTGAAATTAAACATTTAATTTTATTAAGGCAATTGTGGCACACCCCTTGCTTTGTCTTT
ATCAACGCAAATAACAAGTTGATAACAACTTAAGTTT (SEQ ID NO: 7)

PgutA   PgutA-5   5' aaa atc gat gca tca cgc ccc gca caa 3'
                  (SEQ ID NO: 8)
        PgutA-3   5' aaa ctt aag tca gga ttt att gtt tta 3'
                  (SEQ ID NO: 9)
AAAATCGATGCATCACGCCCCGCACAAGGAAGCGGTAGCACTGCCCGATACGGAC
TTTACATAACTCAACTCATTCCCCTCGCTATCCTTTTATTCAAACTTTAAATTAAAATA
TTTATCTTTCATTTTGCGATCAAAATAACACTTTTAAATCTTTCAATCTGATTAGATTAG
GTTGCCGTTTGGTAATAAAACAATAAATCCTGACTTAAGTTT (SEQ ID NO: 10)
```

```
PmelAB2    PmelAB-5-1    5' aaa atc gat gac tgc gag tgg gag cac 3'
                         (SEQ ID NO: 11)
           PmelAB-3      5' aaa ctt aag ggc ttg ctt gaa taa ctt 3'
                         (SEQ ID NO: 12)
```

```
           MelR                                       CRP
AAAATCGATACTCTGCTTTTCAGGTAATTTATTCCCCATAAACTCAGATTTACTGCTGC
TTCACGGAGGATCTGAGTTTATGGGAATGCTCAACCTGGAAGCCGGAGGTTTTCTGCA
GATTCGCCTGCCATGATGAAGTTATTCAAGCAAGCCCTTAAGTTT(SEQ ID NO: 13)
                +1
```

(Binding site for CRP2 is highlighted in light grey and binding sites for MelR are highlited in black)

The fragments were separated by agarose gelelectrophoresis and isolated by the gelextraction kit QiaexII from Qiagen (Hilden, Germany). The isolated fragments were cut with ClaI and AflII and ligated to ClaI/AflII-cut pBW22 (Wilms et al., 2001, Biotechnology and Bioengineering, 73 (2), 95-103). The resulting plasmid containing the melAB2 promoter consisting of the sequence SEQ ID NO. 1 (pBLL7) is shown in FIG. 1. The resulting plasmids containing the prp promoter (pBLL5) and the gutA promoter (pBLL6) are identical except for the promoter region ligated. The sequence of the inserted promoter fragments were confirmed by sequencing (Microsynth GmbH, Balgach, Switzerland).

Example 2

Construction of Fab Fragment Expression Plasmids

Figure 2:
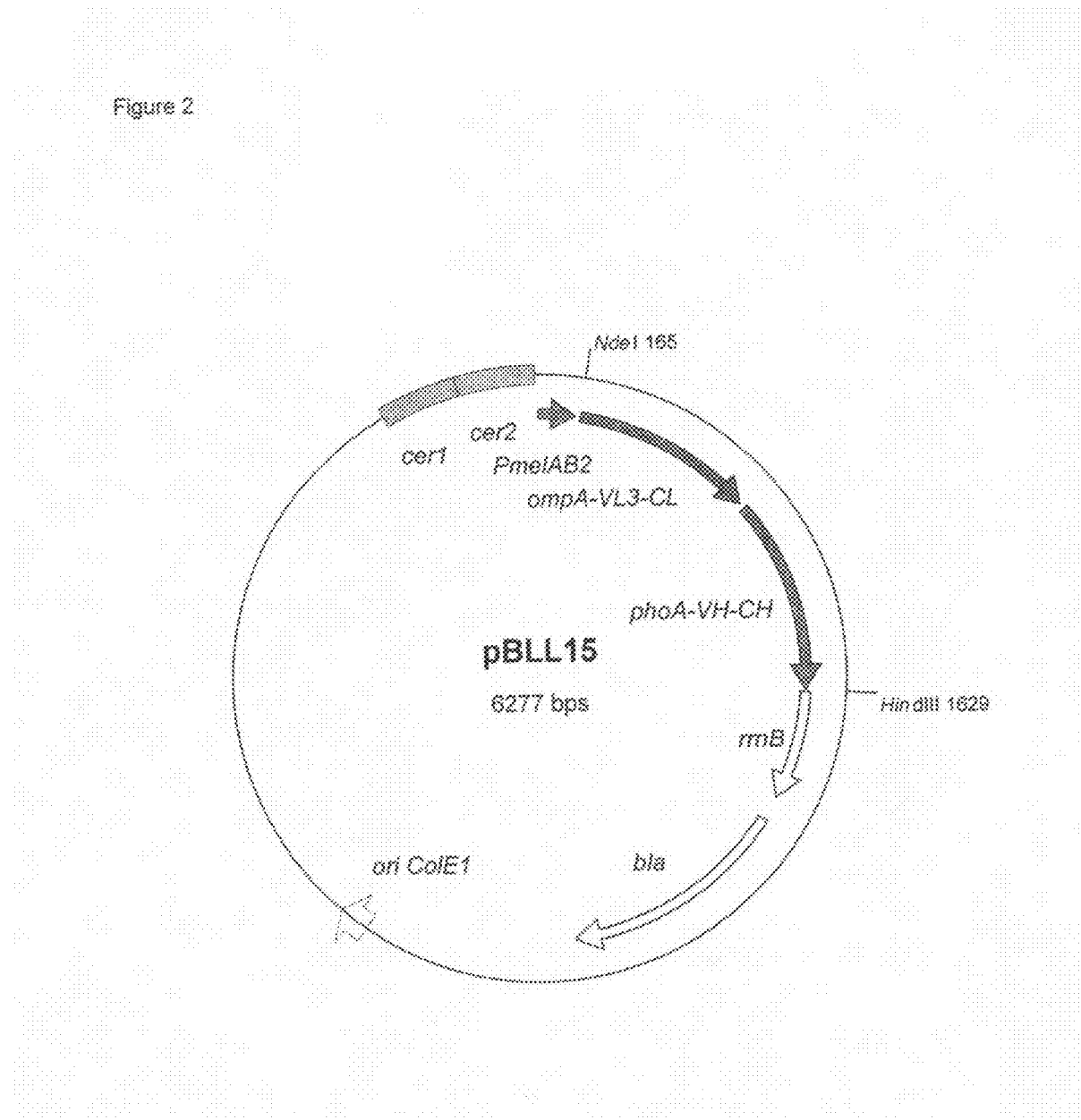
FIG. 2 shows plasmid pBLL15 containing the melibiose inducible promoter (PmelAB2), sequences coding for signal sequences operably linked to the light chain (ompA-VL3-CL) and the heavy chain (phoA-VH-CH) of a Fab-H fragment, and a transcription termination region (rrnB).

As an alternative to an IPTG-inducible lac promoter (plasmid pMx9-HuCAL-Fab-H, Knappik et al., 1985, Gene 33, 103-119), different positively regulated expression systems were analysed for their capacity to produce Fab-H antibody fragments. The Fab-H fragment was amplified out of plasmid pMx9-HuCAL-Fab-H by PCR using the primers Fab-5 (5'-aaa cat atg aaa aag aca gct atc-3'(SEQ ID NO: 14)) and Fab-3 (5'-aaa aag ctt tta tca gct ttt cgg ttc-3' SEQ ID NO: 15)). The PCR-fragment was cut with NdeI and HindIII and inserted into NdeI/HindIII-cut pBW22 to create plasmid pBW22-Fab-H containing the L-rhamnose inducible rhaBAD promoter (Volff et al., 1996, Mol. Microbiol. 21, 1037-1047). The same PCR-fragment was inserted into the different expression plasmids with inducible promoters. The resulting (putative) expression plasmid pBLL15 containing Fab-H and the melAB2 promoter (SEQ ID NO: 3) is shown in FIG. 2. Equivalent plasmids containing the prp promoter (pBLL13) and the gutA promoter (pBLL14) were obtained. The sequence of the Fab-H insert of plasmid pBW22-Fab-H was confirmed by sequencing.

Example 3

Expression of Fab Fragment

Strain W3110 (DSM 5911, Deutsche Sammlung von Mikroorganismen and Zellkulturen GmbH, Braunschweig, Germany) was transformed with the different expression plasmids. The plasmids were isolated from clones which resulted from the different transformations and checked via restriction analysis. Except plasmid pBLL14 all plasmids had the expected restriction pattern. The re-isolated plasmid pBLL14 showed an altered size and restriction pattern which was suggested to be due to recombination events. Therefore strain W3110 (pBLL14) was not tested in the following assays. The remaining strains were tested for their ability to secrete actively folded Fab-H antibody fragments. This productivity test was performed as described in example 4. The following inducers were added in a concentration of 0.2%

| | |
|---|---|
| pBW22-Fab-H | L(+)-Rhamnose monohydrate |
| pBLL13 | Sodium propionate |
| pBLL15 | D(+)-Melibiose monohydrate |
| | D(+)-Raffinose monohydrate |
| | D(+)-Galactose |

Figure 3:
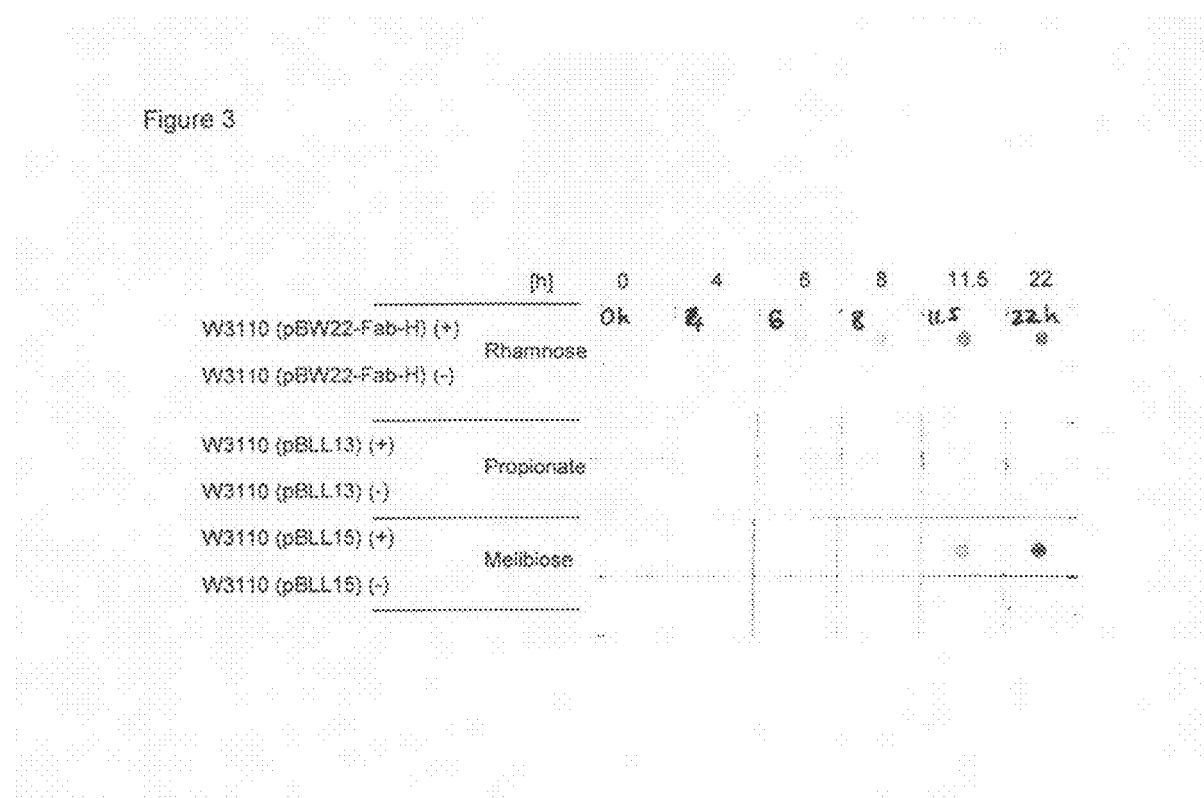
FIG. 3 shows dotblot results (with anti-human light chain for detecting Fab, alkaline peroxidase conjugated) of lysozyme extracts of the uninduced (−) and induced (+) W3110 strains with the different expression plasmids. The time intervals are indicated.

The results from the dot blot experiments are shown in FIG. 3.

to The L-rhamnose- and melibiose-induced strains W3110 (pBW22-Fab-H) and W3110 (pBLL15) showed promising dot blot results: increasing signals over time and almost no background activity. The portion of actively folded antibody fragments was quantified via ELISA. The results are summarized in the following Table 1.

TABLE 1

ELISA results of the W3110 derivatives with the different expression plasmids.

| Plasmid | Inducer | 8 h | 11.5/12 h induced | 22/25 h | 22/25 h uninduced |
|---|---|---|---|---|---|
| in TG1F'- pMx9-HuCAL-Fab-H | IPTG | nd | Nd | 68.64 | 84.56 |
| in W3110 pMx9-HuCAL-Fab-H | IPTG | nd | Nd | 140.56 | 8.14 |
| pBW22-Fab-H | Rhamnose | 176.88 | 259.56 | 328.62 | 6.52 |
| pBLL13 | Propionate | nd | 0.84 | 0.90 | 3.94 |
| pBLL15 | Melibiose | 2.89 | 145.10 | 504.28 | 4.28 |

The time after induction is indicated. The uninduced cultures after 22 or 25 h were measured as uninduced controls and the results from strain W3110 (pMx9-HuCAL-Fab-H) and TG1F'- (pMx9-HuCAL-Fab-H) are used as references. The Fab-H concentration is given in mg/100 OD/L (n.d. not determined)

All strains grew well without any growth inhibition in the presence or absence of the corresponding inducer up to $OD_{600}$ between 4 and 6. The expression plasmids pBW22-Fab-H and pBLL15 led to the highest antibody fragment titers after overnight induction. The melibiose induced strain W3110 (pBLL15) showed a delayed increase in the formation of active antibody fragments compared to the L-rhamnose (pBW22-Fab-H) induced system.

The L-rhamnose inducible strain W3110 (pBW22-Fab-H) was tested in the Respiration Activity Monitoring System (RAMOS, ACBiotec, Jillich, Germany), a novel measuring system for the on-line determination of respiration activities in shake flasks. In comparison to the normal shake flask experiment the antibody titer (which was measured via ELISA) doubled (703.64 mg/L/100 $OD_{600}$ after 23 h of induction). The optimised growth using the RAMOS equipment favours the production of active antibody fragments.

Example 4

Melibiose Induction in Shake Flasks

*E. coli* W3110 carrying plasmid pBLL15 was tested for its capacity to produce actively folded Fab-H antibody fragments. Overnight cultures [in NYB medium (10 g/l tryptone, 5 g/l yeast extract, 5 g/l sodium chloride) supplemented with 100 µg/ml of Ampicillin, 37° C.] were diluted (1:50) in 20 ml of fresh glycerol medium (as described by Kortz et al., 1995, J. Biotechnol. 39, 59-65, whereas the vitamin solution was used as described by Kulla et al., 1983, Arch. Microbiol, 135, 1 and incubated at 30° C. Melibiose (0.2%) was added when the cultures reached an $OD_{600}$ of about 0.4. Samples (1 ml) were taken at different time intervals, centrifuged and the pellets were stored at −20° C. The frozen cells were lysed according to the above described lysozyme treatment and the supernatants were analysed in dot blot and ELISA assays. 504.28 mg/L/100 $OD_{600}$ of functional Fab-H antibody fragments were obtained.

Example 5

Occurence of High Molecular Weight Aggregates

Figure 4:
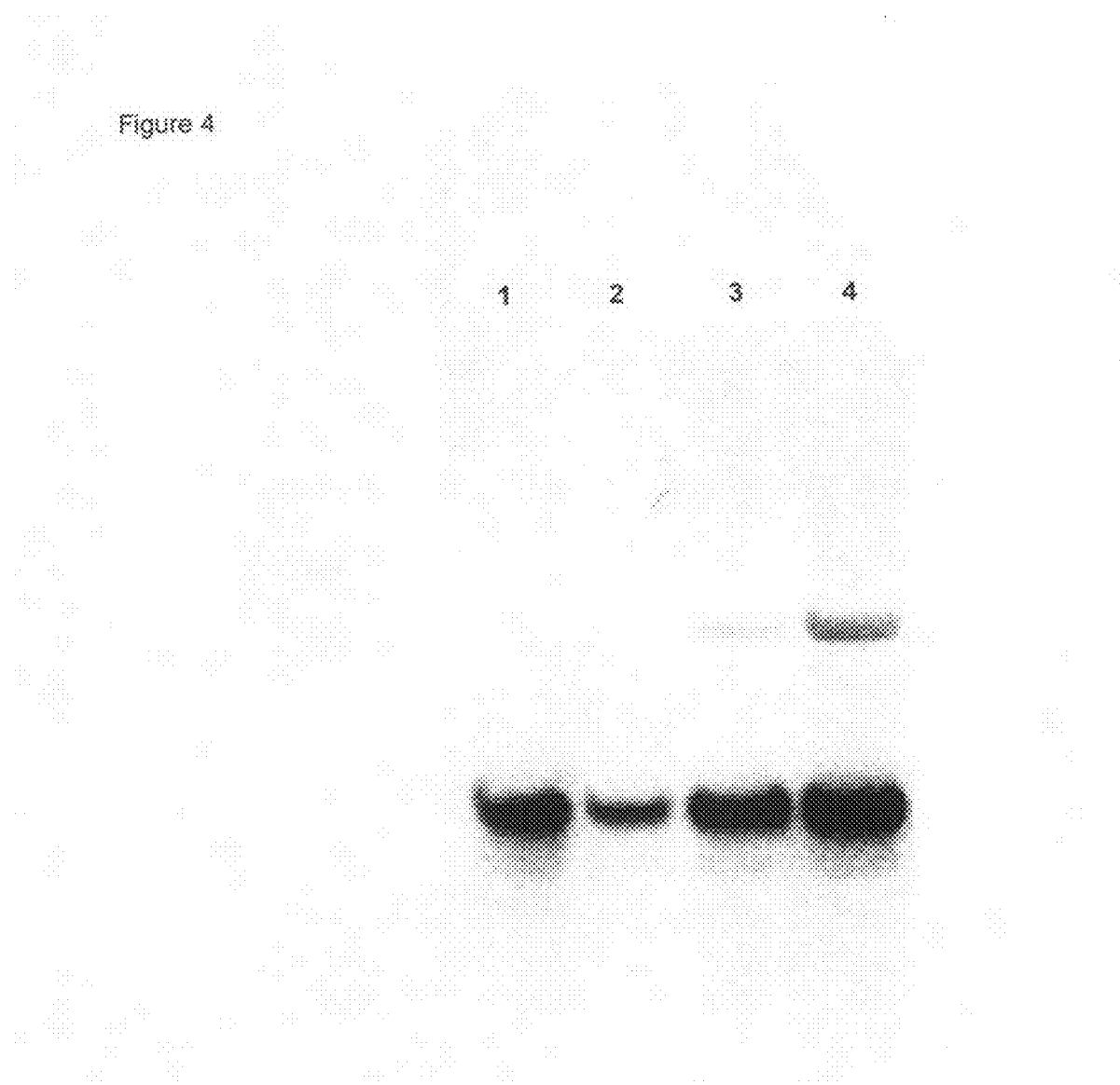
FIG. 4 shows Western blot of lysozyme extracts of strains W3110 (pBLL15) using an anti-human light chain for detecting Fab, alkaline peroxidase conjugated (lane 1: Reference Fab-H (2 µg); lane 2: W3110 (pBLL15), induced, 9 h; lane 3: W3110 (pBLL15), induced, 12 h; lane 4: W3110 (pBLL15), induced, 23 h).

In order to find out if high molecular weight aggregates are produced, western blot of extracts of strain W3110 (pBLL15), which showed the highest antibody titer (Table 1), was conducted using the anti-human Fab-H+AP conjugate. The culture was performed as described in example 4. Samples were taken after 9, 12 and 23 hours after induction with melibiose. Western blot of lysozyme extracts of strains W3110 (pBLL15) using the anti-human Fab-H+AP conjugate is shown in FIG. 4. Lower concentrations of high molecular weight aggregates correspond to higher titers of functional antibody fragments.

The choice of the expression system seems to influence the way in which the antibody fragments are formed: functional or in aggregates.

Example 6

Influence of Signal Peptides

The genome database of *E. coli* was used to look for useful signal peptides that could be used in combination with the Fab-H fragments VL3-CL and VH-CH. The signal sequences from periplasmic binding proteins for sugars, amino acids, vitamins and ions were chosen. These periplasmic proteins represent a relatively homogeneous group that have been more extensively studied than other periplasmic proteins. Since they are generally abundant their signal sequences have to ensure an efficient transport over the inner membrane into the periplasm. All possible signal peptide Fab combinations were checked for their sequence peptide and cleavage site probability using the SignalP web server (http://www.cbs.d-tu.dk/services/SignalP-2.0/#submission) as shown in the following Table 2.

| Signal peptide (discloses SEQ ID NOS 16-64, respectively, in order of appearance) | | Signal peptide probability | Max Cleavage Site Probability |
|---|---|---|---|
| OmpA (*E. coli*)-Outer membrane protein a precursor | | | |
| MKKTA IAIAV ALAGF ATVAQ A | APKDN (OmpA) | 1.000 | 0.993 |
| MKKTA IAIAV ALAGF ATVAQ A | DIELT (OmpA-VL3-CL, Fab-H) | 1.000 | 0.971 |
| PhoA (*E. coli*)-Alkaline phosphatase precursor | | | |
| VKQST IALAL LPLLF TPVTK A | RTPEM (PhoA) | 0.996 | 0.765 |
| MKQST IALAL LPLLF TPVTK A | QVQLK (PhoA-VH-CH, Fab-H) | 0.999 | 0.784 |
| PelB (*Erwinia chrysantemi*)-Pectate lyase precursor | | | |
| MKSLI TPITA GLLLA LSQPL LA | ATDTG (PelB) | 1.000 | 0.999 |
| MKSLI TPITA GLLLA LSQPL LA | DIELT (PelB-VL3-CL, Fab-H) | 1.000 | 0.998 |
| MKSLI TPITA GLLLA LSQPL LA | QVQLK (PelB-VH-CH, Fab-H) | 1.000 | 0.998 |
| PelB (*Erwinia carotovora*)-Pectate lyase precursor | | | |
| MKYLL PTAAA GLLLL AAQPA MA | ANTGG (PelB) | 1.000 | 1.000 |
| MKYLL PTAAA GLLLL AAQPA MA | DIELT (PelB-VL3-CL, Fab-H) | 1.000 | 1.000 |
| MKYLL PTAAA GLLLL AAQPA MA | QVQLK (PelB-VH-CH, Fab-H) | 1.000 | 1.000 |
| PelB (*Xanthomonas campestris*)-Pectate lyase precursor | | | |
| MKPKF STAAA ASLFV GSLLV IGVAS A | DPALE (PelB) | 1.000 | 0.993 |
| MKPKF STAAA ASLFV GSLLV IGVAS A | DIELT (PelB-VL3-CL, Fab-H) | 1.000 | 0.985 |
| MKPKF STAAA ASLFV GSLLV IGVAS A | QVQLK (PelB-VH-CH, Fab-H) | 1.000 | 0.988 |

| Signal peptide (discloses SEQ ID NOS 16-64, respectively, in order of appearance) | | Signal peptide probability | Max Cleavage Site Probability |
|---|---|---|---|
| LamB (*E. coli*)-Maltoporin precursor (Lambda receptor protein) | | | |
| MMITL RKLPL AVAVA AGVMS AQAMA | VDFHG (LamB) | 1.000 | 0.975 |
| MMITL RKLPL AVAVA AGVMS AQAMA | DIELT (LamB-VL3-CL, Fab-H) | 1.000 | 0.979 |
| MM/TL RKLPL AVAVA AGVMS AQAMA | QVQLK (LamB-VH-CH, Fab-H) | 1.000 | 0.988 |
| MalE (*E. coli*)-Maltose-binding protein precursor | | | |
| MKIKT GARIL ALSAL TTMMF SASAL A | KIEEG (MalE) | 1.000 | 0.956 |
| MKIKT GARIL ALSAL TTMMF SASAL A | DIELT (MalE-VL3-CL, Fab-H) | 1.000 | 0.978 |
| MKIKT GARIL ALSAL TTMMF SASAL A | QVQLK (MalE-VH-CH, Fab-H) | 1.000 | 0.990 |
| Bla (pBR322) (*E. coli*)-Beta-lactamase | | | |
| MSIQH FRVAL IPFFA AFCLP VFA | HPETL (Bla) | 1.000 | 1.000 |
| MSIQH FRVAL IPFFA AFCLP VFA | DIELT (Bla-VL3-CL, Fab-H) | 1.000 | 1.000 |
| MSIQH FRVAL IPFFA AFCLP VFA | QVQLK (Bla-VH-CH, Fab-H) | 1.000 | 0.999 |
| OppA (*E. coli*)-Periplasmic oligopeptide-binding protein | | | |
| MTNIT KRSLV AAGVL AALMA GNVAL A | ADVPA (OppA) | 1.000 | 0.996 |
| MTNIT KRSLV AAGVL AALMA GNVAL A | DIELT (OppA-VL3-CL, Fab-H) | 1.000 | 0.911 |
| MTNIT KRSLV AAGVL AALMA GNVAL A | QVQLK (OppA-VH-CH, Fab-H) | 1.000 | 0.984 |
| TreA (*E. coli*)-Periplasmic trehalase precursor (Alpha-trehalose glucohydrolase) | | | |
| MKSPA PSRPQ KMALI PACIF LCFAA LSVQA | EETPV (TreA) | 1.000 | 0.996 |
| MKSPA PSRPQ KMALI PACIF LCFAA LSVQA | DIELT (TreA-VL3-CL, Fab-H) | 1.000 | 0.961 |
| MKSPA PSRPQ KMALI PACIF LCFAA LSVQA | QVQLK (TreA-VHCH, Fab-H) | 1.000 | 0.989 |
| MppA (*E. coli*)-Periplasmic murein peptide-binding protein precursor | | | |
| MKHSV SVTCC ALLVS SISLS YA | AEVPS (MppA) | 1.000 | 0.943 |
| MkHSV SVTCC ALLVS SISLS YA | DIELT (MppA-VL3-CL, Fab-H) | 1.000 | 0.906 |
| MEHSV SVTCC ALLVS SISLS YA | QVQLK (MppA-VH-CH, Fab-H) | 1.000 | 0.938 |
| BglX (*E. coli*)-Periplasmic beta-glucosidase precursor | | | |
| MKWLC SVGIA VSLAL QPALA | DDLFG (BglX) | 1.000 | 0.999 |
| MKWLC SVGIA VSLAL QPALA | DIELT (BglX-VL3-CL, Fab-H) | 0.999 | 0.999 |
| MKWLC SVGIA VSLAL QPALA | QVQLK (BglX-VH-CH, Fab-H) | 1.000 | 0.996 |
| ArgT (*E. coli*)-Lysine-arginine-ornithine-binding periplasmic protein precursor | | | |
| MKKSI LALSL LVGLS TAASS YA | ALPET | 1.000 | 0.929 |
| MKKSI LALSL LVGLS TAASS YA | DIELT (ArgT-VL3-CL, Fab-H) | 1.000 | 0.947 |
| MKKSI LALSL LVGLS TAASS YA | QVQLK (ArgT-VH-CH, Fab-H) | 1.000 | 0.960 |
| MalS (*E. coli*)-Alpha-amylase precursor | | | |
| MKLAA CFLTL LPGFA VA | ASWTS (MalS) | 1.000 | 0.794 |
| MKLAA CFLTL LPGFA VA | DIELT (MalS-VL3-CL, Fab-H) | 0.998 | 0.995 |
| MKLAA CFLTL LPGFA VA | QVQLK (MalS-VH-CH, Fab-H) | 1.000 | 0.990 |
| HisJ (*E. coli*)-Histidine-binding periplasmicprotein precursor | | | |
| MKKLV LSLSL VLAFS SATAA FA | AIPQN (HisJ) | 1.000 | 0.994 |
| MKKLV LSLSL VLAFS SATAA FA | DIELT (HisJ-VL3-CL, Fab-H) | 1.000 | 0.957 |
| MKKLV LSLSL VLAFS SATAA FA | QVQLK (HisJ-VH-CH, Fab-H) | 1.000 | 0.988 |
| XyF (*E. coli*)-D-Xylose-binding periplasmic protein precursor | | | |
| MKIKN ILLTL CTSLL LTNVA AHA | KEVKI (XylF) | 1.000 | 0.996 |
| MKIKN ILLTL CTSLL LTNVA AHA | DIELT (XylF-VL3-CL, Fab-H) | 1.000 | 0.992 |
| MKIKN ILLTL CTSLL LTNVA AHA | QVQLK (XylF-VH-CH, Fab-H) | 1.000 | 0.996 |

| Signal peptide (discloses SEQ ID NOS 16-64, respectively, in order of appearance) | | Signal peptide probability | Max Cleavage Site Probability |
|---|---|---|---|
| FecB (E. coli)-Iron(III) dicitrate-binding periplasmic protein precursor | | | |
| MLAFI RFLFA GLLLV ISHAF A | ATVQD (FecB) | 1.000 | 0.975 |
| MLAFI RFLFA GLLLV ISHAF A | DIELT (FecB-VL3-CL, Fab-H) | 1.000 | 0.989 |
| MLAFI RFLFA GLLLV ISHAF A | QVQLK (FecB-VH-CH, Fab-H) | 1.000 | 0.990 |

The following six combinations were chosen:

LamB-VL3-CL (Maltoporin precursor)

MalE-VH-CH (Maltose-binding protein precursor)

Bla-VL3-CL (Beta-lactamase)

TreA-VH-CH (Periplasmic trehalase precursor)

ArgT-VL3-CL (Lysine-arginine-ornithine-binding periplasmic protein precursor)

FecB-VH-CH (Iron CR dicitrate-binding periplasmic protein precursor

The gene fusions to generate signal peptide (SP) to VL3-CL and VH-CH fusions were carried out with overlapping PCR primers and are summarized in the following amplification Table 3

| Primer | Template | Fragment |
|---|---|---|
| LamB-VL3-CL | | |
| lamB-5 Lamb-3 | Genomic DNA of E. coli W3110 | lamB-SP |
| lamB-VL3-5 VL3-3 | pMx9-HuCAL-Fab-H-S-S | VL3-CL |
| lamB-5 VL3-3 | lamB-SP/VL3-CL | lamB-VL3-CL |
| MalE-VH-CH | | |
| malE-5 male-3 | Genomic DNA of E. coli W3110 | malE-SP |
| malE-VH-CH VH-3 | pMx9-HuCAL-Fab-H | VH-CH |
| malE-5 VL3-3 | malE-SP/VH-CH | malE-VH-CH |
| Bla-VL3-CL | | |
| bla-5 bla-3 | Genomic DNA of E. coli W3110 | bla-SP |
| bla-VL3-5 VL3-3 | pMx9-HuCAL-Fab-H-S-S | VL3-CL |
| bla-5 VL3-3 | bla-SP/VL3-CL | bla-VL3-CL |
| TreA-VH-CH | | |
| treA-5 treA-3 | Genomic DNA of E. coli W3110 | treA-SP |
| treA-VH-CH VH-3 | pMx9-HuCAL-Fab-H-S-S | VH-CH |
| treA-5 VH-3 | treA-SP/VH-CH | treA-VH-CH |
| ArgT-VL3-CL | | |
| argT-5 argT-3 | Genomic DNA of E. coli W3110 | argT-SP |
| argT-VL3-5 VL3-3 | pMx9-HuCAL-Fab-H | VL3-CL |
| argT-5 VL3-3 | argT-SP/VL3-CL | argT-VL3-CL |
| FecB-VH-CH | | |
| fecB-5 fecB-3 | Genomic DNA of E. coli W3110 | fecB-SP |
| fecB-VH-CH VL3-3 | pMx9-HuCAL-Fab-H-S-S | VH-CH |
| fecB-5 VL3-3 | fecB-SP/VH-CH | fecB-VH-CH |

The fusions of the signal peptide sequences with the VL3-CL and VH-CH sequences were performed as described elsewhere (Horton, R. M., Hunt, H. D., Ho, S. N., Pullen, J. K. and Pease, L. R. (1989) Engineering hybrid genes without the use of restriction enzymes: gene splicing by overlap extension. Gene 77, 61-68). The SP-VL3-CL genes were cut with restriction enzymes NdeI and PstI and ligated into NdeI/PstI cut pBW22 and into pBLL7.

Figure 5:
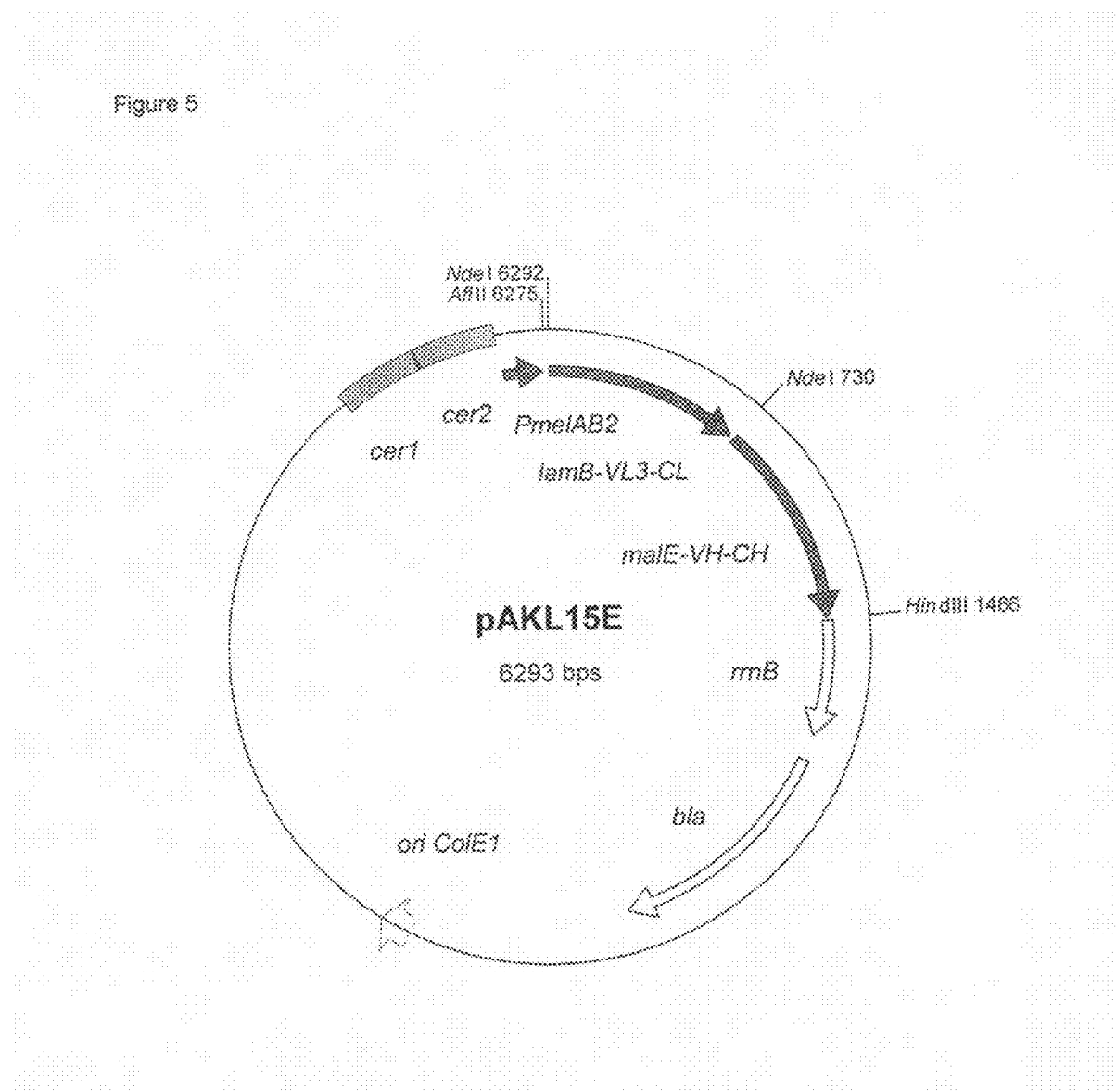
FIG. 5 shows plasmid pAKL15E containing the melibiose inducible promoter (PmelAB2) and the Fab-H genes with altered signal sequences.

The resulting plasmids were cut with PstI and HindIII and ligated to PstI/HindIII cut SP-VH-CH genes. Since the integration of the bla-VL3-CL and fecB-VH-CH genes was not possible only the Fab-H expression plasmid containing the lamB-VL3-CL and malE-VH-CH genes could be tested. A lamB-VL3-CL/malE-VH-CH expression plasmid containing the L-rhamnose inducible promoter (pAKL14) was obtained. The lamB-VL3-CL/malE-VH-CH genes which were isolated from plasmid pAKL15 (example 7) as AflII/HindIII fragment were ligated into AflII/HindIII-cut pBLL7 to obtain pAKL15E. FIG. 5 illustrates the expression plasmid pAKL15E containing the melibiose inducible promoter and lamB-VL3-CL/malE-VH-CH (SEQ ID. NO. 4).

Example 7

Influence of Translation Initiation Regions on Fab Expression

The Fab-H genes of plasmid pAKL14 and plasmid pAKL15E contain the same DNA sequence 5' of the start codon (translation initiation region) whereas in the original plasmid pMx9-HuCAL-Fab-H the translation initiation regions of both Fab-H genes are different. A comparison of the translation initiation regions sequences of plasmid pMx9-HuCAL-Fab-H and pAKL14/pAKL15E is shown in the following Table 4:

```
pMx9-HuCAL-Fab-H
ompA-VL3-CL        gagggcaaaaa   atg
                   (SEQ ID NO: 65)

phoA-VH-CH         aggagaaataaa  atg
                   (SEQ ID NO: 66)
```

-continued pAKL14/pAKL15E lamB-VL3-CL          aggagatatacat atg
                     (SEQ ID NO: 67)

malE-VH-CH           aggagatatacat atg
                     (SEQ ID NO: 67)

The productivity of strain W3110 (pAKL14) was tested in shake flasks as described in example 4. The strain grew well in the presence or absence of L-rhamnose. That means the production of Fab-H did not influence the viability of the cells.

The new signal peptide constructs (in combination with the modified translation initiation signals) again increased the antibody fragment titer from 328.62 mg/L/100 $OD_{600}$ (plasmid pBW22-Fab-H which contains the MOR gene construct from plasmid pMx9-HuCAL-Fab-H) to 596.14 mg/L/100 $OD_{600}$ (plasmid pAKL14) and to 878.86 mg/L/100 $OD_{600}$ (plasmid pAKL15E). The sequencing of the lamB-VL3-CL and malE-VH-CH genes in pAKL14 revealed three base exchanges which are supposed to be due to the construction of the fusion genes by two consecutive PCR reactions. The base exchanges led to the following amino acid changes (the wrong amino acids are emphasized):

```
VL3-CL (pAKL14)-pI = 4.85
MMITLRKLPLAVAVAAGVMSAQAMADIELTQPPSVSVAPGQTARISCSGN

ALGDKYASWYQQNPGQAPVLVIYDDSDRPSGIPERFSGSNSGNTATLTIS

GTQAEDEADYYCQSYDSPQVVFGGGTKLTVLGQPKAAPSVTLFPPSSEEL

QANKATLVCLISDFYPGAVTVAWKADSSPVKAGVETTTPSKQSNNKYAAS

SYLSLTPEQWKSHRSYSCQVTHEGSTVEKTVAPTEA
(SEQ ID NO: 68)

VH-CH (pAKL14)-pI = 9.52
MKIKTGARILALSALTTMMFSASALAQVQLKESGPALVKPTQTLTLTCTF

SGFSLSTSGVGVGWIRQPPGKALEWLALIDWDDDKYYSTSLKTRLTISKD

TSKNQVVLTMTNMDPVDTATYYCARYPVTQRSYMDVWGQGTLVTVSSAST

KGPSVLPLAPSSKSTSGGTAALGCLVKDYFPEPVTVSWNSGALTSGVHTF

PAVLQSSGLYSLSSVVTVPSSSLGTQTYICNVNHKPSNTKVDKKVEPKS
(SEQ ID NO: 69)
```

The light chain of Fab-H carries two mistakes (D50N, K63N) and the heavy chain one amino acid exchange (F156L). To restore the original Fab-H sequence two fragments from plasmid pAKL14 (138 by SexAI/BamHI and 310 by BssHII/HindIII fragment) were exchanged against the homologous fragments of plasmid pBW22-Fab-H (which carries the unchanged Fab-H gene sequence). The resulting plasmid pAKL15 carries the correct Fab-H sequence. The exchange of the three amino acids had no apparent effect on the overall Fab-H properties since the pI was unchanged. Therefore the capacity of strain W3110 (pAKL15) to produce functional Fab-H antibody fragments was supposed to be similar to strain W3110 (pAKL14) and was not analysed.

The Fab-H antibody fragment productivity could be increased by using different optimisation strategies. The following Table 5 summarizes the improvements:

| Strain | Improvement | Concentration of functional Fab-H Antibody (mg/L/100 OD) | Activity increase |
|---|---|---|---|
| TG1F'- (pMx9-HuCAL-Fab-H) | MOR strain | 84.56 | |
| W3110 (pMx9-HuCAL-Fab-H) | Strain background | 140.45 | 1.7 |
| W3110 (pBW22-Fab-H) | Expression system (Rhamnose) | 328.62 | 3.9 |
| W3110 (pBLL15) | Expression system (Melibiose) | 504.28 | 6 |
| W3110 (pAKL14) | Signal peptide Translation (Rhamnose) | 596.14 | 7 |
| W3110 (pAKL15E) | Signal peptide Translation (Melibiose) | 878.86 | 10.4 |

Figure 6:
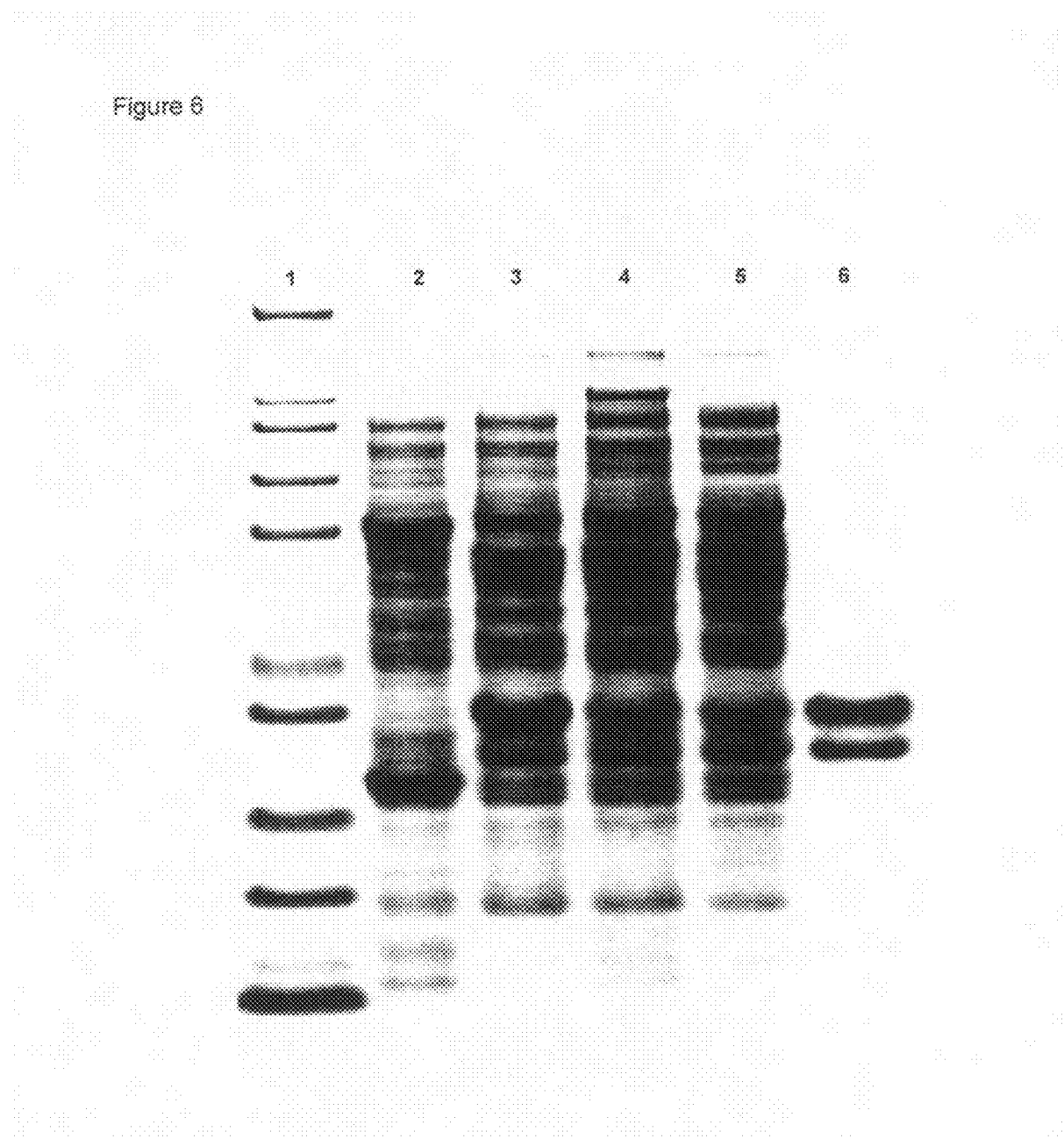
FIG. 6 shows SDS-PAGE of lysozyme extracts of different W3110 strains with high Fab-H antibody concentrations. The strains producing the light and heavy chain without signal sequences are used as a negative reference (lane 1: Marker; lane 2: W3110 (pMx9-HuCAL-Fab-H); lane 3: W3110 (pBW22-Fab-H); lane 4: W3110 (pBLL15), lane 5: W3110 (pAKL14); lane 6: Standard (2 µg)).

Strains which produced high Fab-H antibody titers were analysed via SDS-PAGE (FIG. 6). The highest functional Fab-H concentrations were measured in strains which produce a balanced amount of light and heavy chain (lanes 4 and 5). The L-rhamnose inducible strains which carry the Fab-H fragment such as W3110 (pBW22-Fab-H) (lane 3) strongly overproduce the light chain.

Example 8

Melibiose Induction in Shake Flasks

Figure 8:
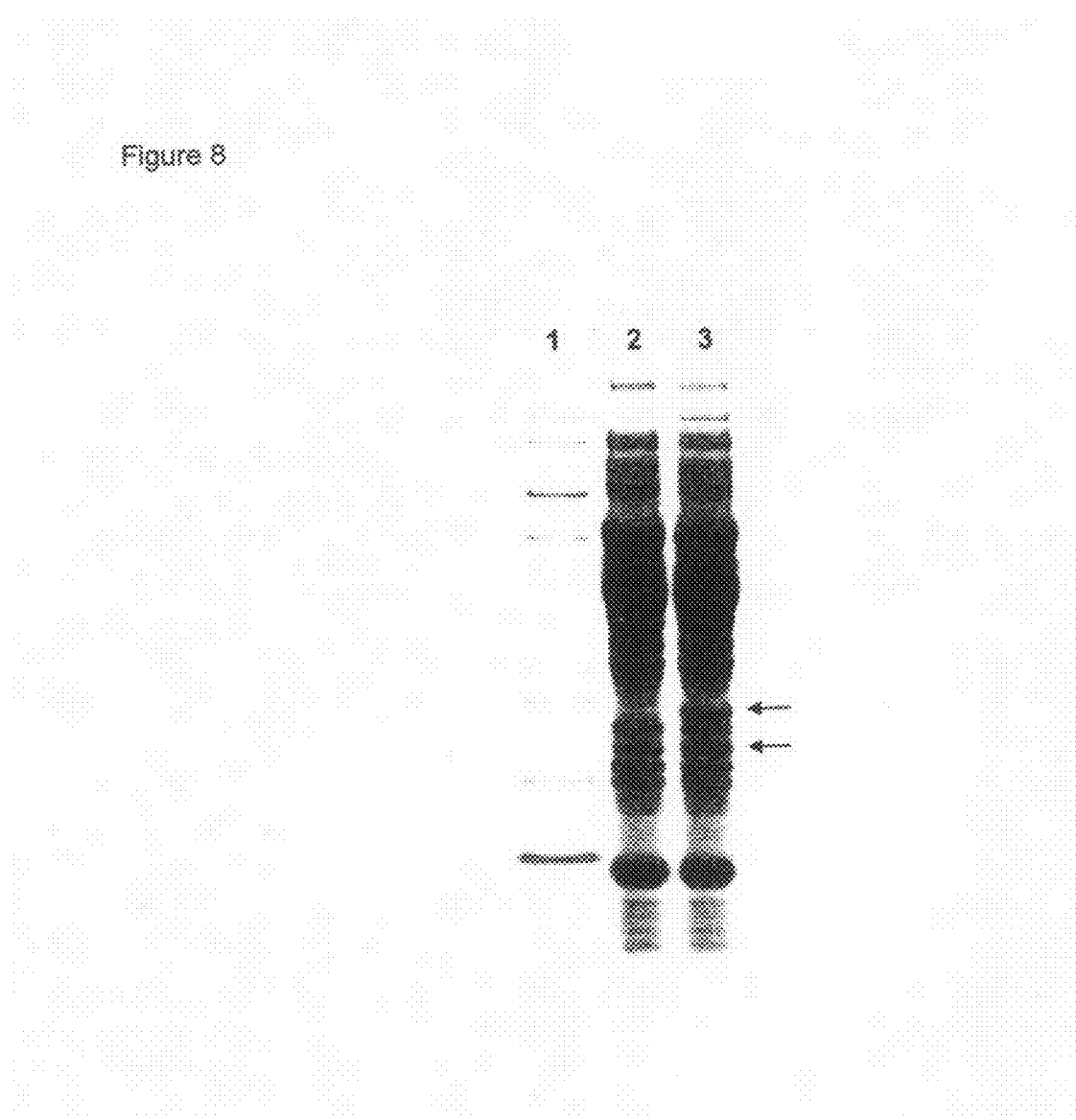
FIG. 8 shows SDS-PAGE of lysozyme extracts of strain W3110 (pAKL15E) in the presence or absence of the inducer melibiose. The position of the light and heavy chain is indicated (lane 1: Marker; lane 2: W3110 (pAKL15E), not induced; lane 3: W3110 (pAKL15E), induced).

E. coli W3110 carrying plasmid pAKL15E was tested for its capacity to produce actively folded Fab-H antibody fragments. Overnight cultures [in NYB medium (10 g/l tryptone, 5 g/l yeast extract, 5 g/l sodium chloride) supplemented with 100 µg/ml of Ampicillin, 37° C.] were diluted (1:50) in 20 ml of fresh glycerol medium (as described by Kortz et al., 1995, J. Biotechnol. 39, 59-65, whereas the vitamin solution was used as described by Kulla et al., 1983, Arch. Microbiol, 135, 1 and incubated at 30° C. Melibiose (0.2%) was added when the cultures reached an $OD_{600}$ of about 0.4. Samples (1 ml) were taken at different time intervals, centrifuged and the pellets were stored at −20° C. The frozen cells were lysed according to the above described lysozyme treatment and the supernatants were analysed in SDS-PAGE and ELISA assays. The melibiose inducible strain which carry the Fab-H genes with the altered signal peptides (lamB-VL3-CL/malE-VH-CH) showed the highest Fab-H antibody titers (Table 5). The light and heavy chain of Fab-H were produced in equal amounts (FIG. 8).

Example 9

Figure 7:
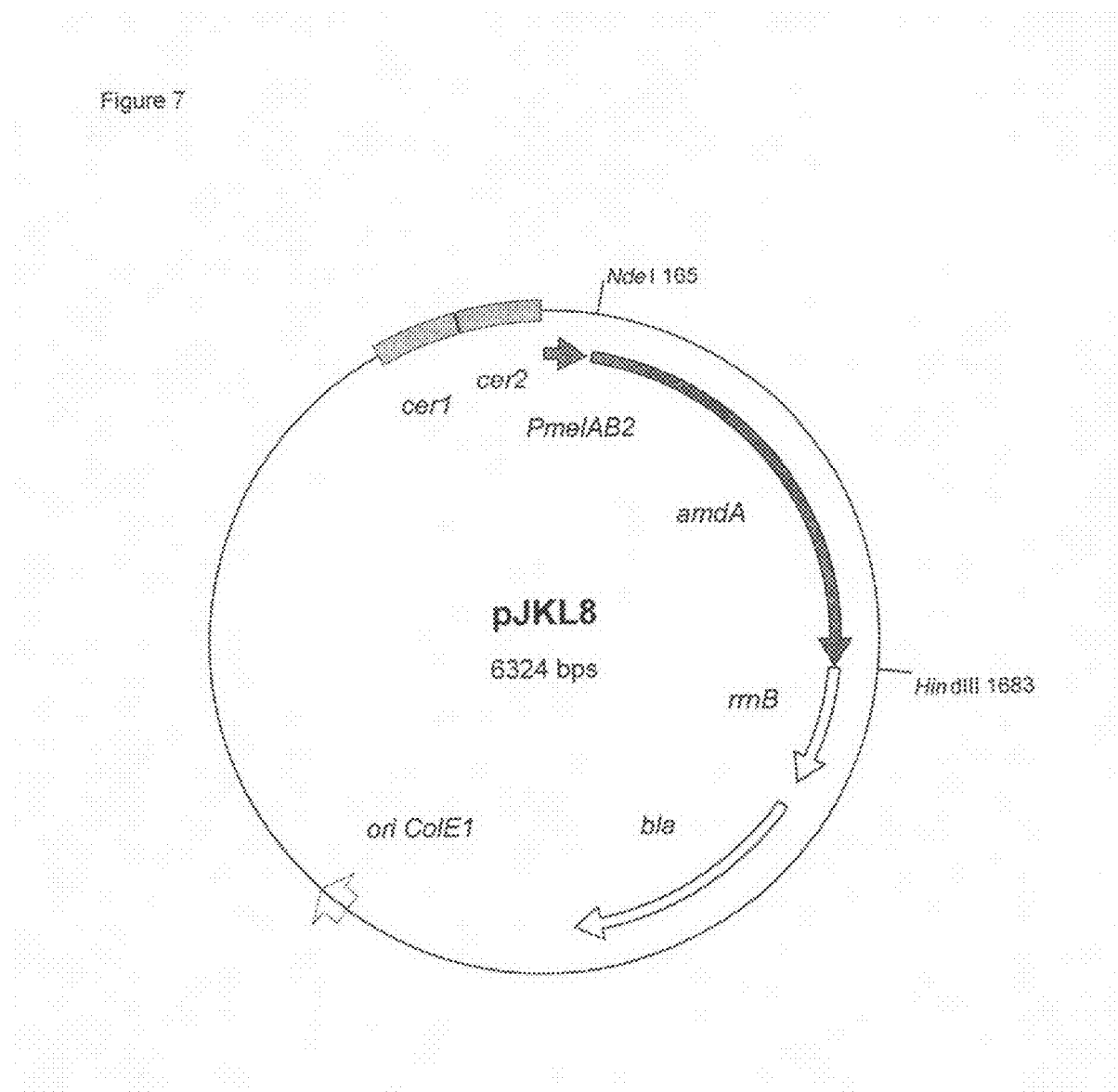
FIG. 7 shows plasmid pJKL8 containing the melibiose inducible promoter (PmelAB2) and a sequence coding for an amidase from strain KIE153 (Burkholderia sp. DSM9925), and a transcription termination region (rrnB).

Melibiose Induction of an Amidase from Strain KIE153 (Burkholderia sp. DSM9925) in Shake Flasks E. coli W3110 carrying plasmid pJKL8 (FIG. 7) was tested for its capacity to convert racemic piperazine-2-carboxamide to (R)-piperazine-2-carboxylic acid. Overnight cultures [in NYB medium (10 g/l tryptone, 5 g/l yeast extract, 5 g/l sodium chloride) supplemented with 100 µg/ml of Ampicillin, 30° C.] were diluted (1:50) in 20 ml of fresh glycerol medium (as described by Kortz et al., 1995, J. Biotechnol. 39, 59-65, whereas the vitymin solution was used as described by Kulla et al., 1983, Arch. Microbiol, 135, 1 and incubated at 30° C. Melibiose (0.2%) was added when the culture reached an OD600 of about 0.8.

After an induction time of 19 h the cells were harvested and stored at −20° C. Amidase activity was tested as described in Eichhorn et al. 1997, Tetrahedron Asymmetry, 8(15), 2533-36. The resting cells enantioselectively converted (R)-piperazine-2-carboxamide to (R)-piperazine-2-carboxylic acid with a conversion rate of about 1 g/h/$OD_{600}$.

Example 10

Melibiose Induction of a Single Chain Antibody (ScFv, S1) in Shake Flasks

Figure 9:
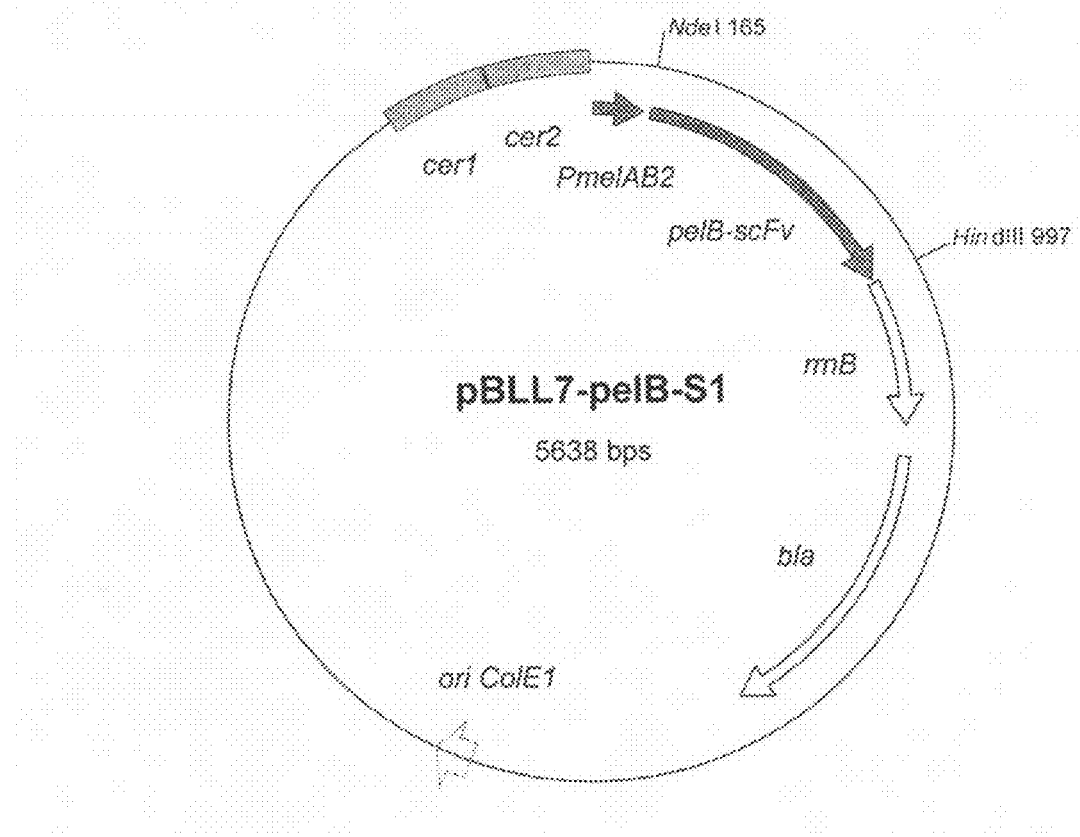
FIG. 9 shows plasmid pBLL7-pelB-S1 containing the melibiose inducible melAB2 promoter and a sequence coding for a single chain antibody (scFv, S1). The sequence coding for S1 is preceded by a sequence coding for a PelB signal peptide.
Figure 10:
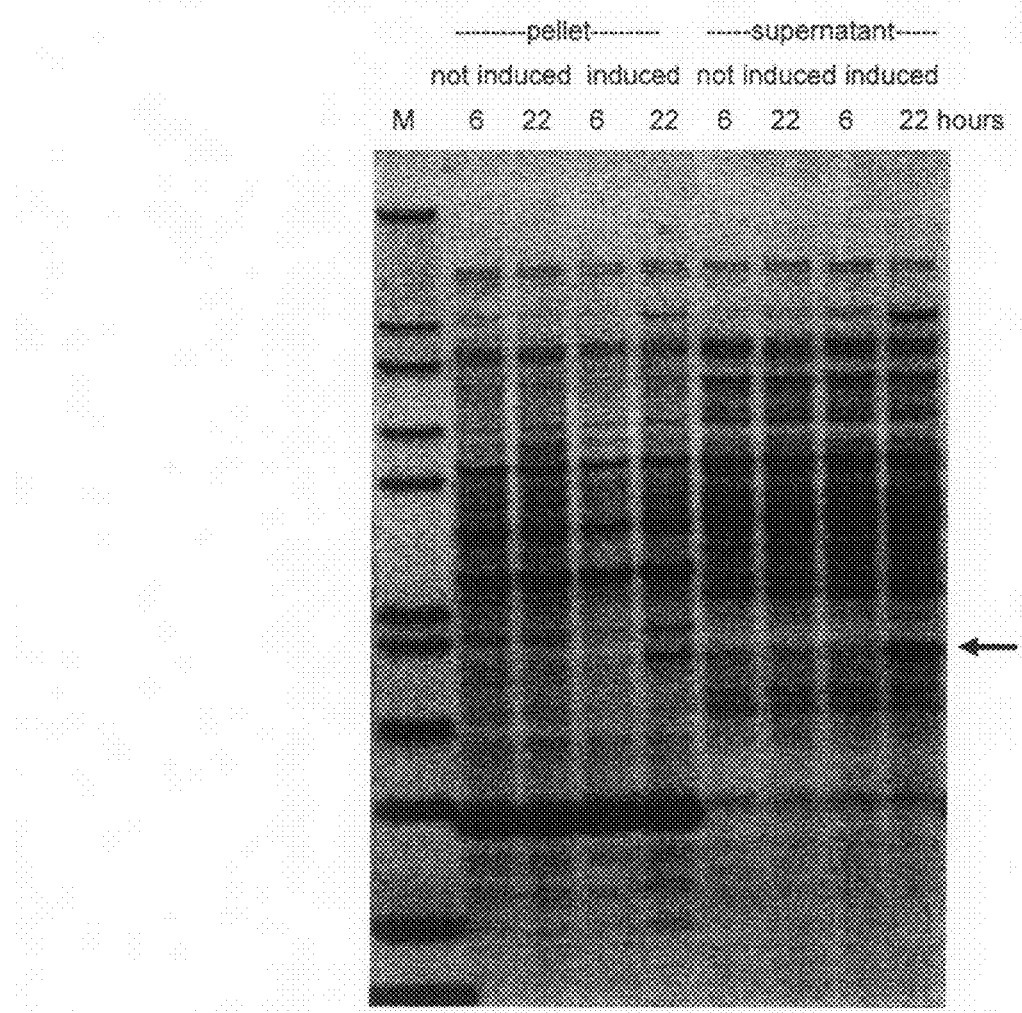
FIG. 10 shows SDS-PAGE of crude extracts of not induced (−) and (+) strain W3110 (pBLL7-pelB-S1). Samples were taken at different time intervals as indicated. The soluble and insoluble protein fractions after lysozyme treatment were analyzed. An arrow indicates the scFv protein. M=Mark12, molecular weight standard of Invitrogen.

The scFv gene was isolated via PCR using the primers 5-S (5'-aaa cat atg aaa tac cta ttg cct acg gc-3'(SEQ ID NO: 70)) and 3-S1 (5'-aaa aag ctt act acg agg aga cgg-3'(SEQ ID NO: 71)). The corresponding S1 protein contains a PelB signal sequence which is responsible for transport of the protein to the periplasm of E. coli. The PCR-fragment was cut with NdeI and HindIII and inserted into NdeI/HindIII-cut pBLL7 to create plasmid pBLL7-pelB1-S1 containing the melibiose inducible melAB2 promoter (FIG. 9). The sequence of the S1 insert of plasmid pBLL7-S1 was confirmed by sequencing. Strain W3110 (DSM 5911, Deutsche Sammlung von Mikroorganismen and Zellkulturen GmbH, Braunschweig, Germany) was transformed with plasmid pBLL7-pelB1-S1. The plasmids were isolated from different clones and verified by restriction analysis. E. coli W3110 (pBLL7-pelB-S1) was tested for its capacity to produce soluble S1. Overnight cultures [in NYB medium (10 g/l tryptone, 5 g/l yeast extract, 5 g/l sodium chloride) supplemented with 100 μg/ml of Ampicillin, 37° C.] were diluted (1:50) in 20 ml of fresh glycerol medium [as described by Kortz et al., 1995, J. Biotechnol. 39, 59-65, with the exception of the vitamin solution (as described by Kulla et al., 1983, Arch. Microbiol, 135, 1)] and incubated at 30° C. Melibiose (0.2%) was added when the cultures reached an $OD_{600}$ of about 0.4. Samples (1 ml) were taken at different time intervals, centrifuged and the pellets were stored at −20° C. The frozen cells were lysed according to the above described lysozyme treatment and the supernatants and insoluble protein pellets were analysed via SDS-PAGE (FIG. 10) and Bioanalyzer. Most of the S1 protein (1.7 g/Lx mg/L100 $OD_{600}$) was produced in the soluble protein fraction.

The invention claimed is:

1. A vector expressible in a prokaryotic host comprising the melAB promoter of the melibiose operon operably linked to a transcriptional unit comprising a nucleic acid sequence encoding an antibody, and a prokaryotic signal sequence operably linked to said nucleic acid sequence, wherein the expression of said nucleic acid sequence is controlled by said melAB promoter, wherein said melAB promoter is deficient in the CRP1 binding site and wherein said melAB promoter consists of the sequence of SEQ ID NO: 1 or a sequence complementary thereof.

2. The vector of claim 1, wherein said transcriptional unit further comprises a translation initiation region upstream of the initiation point of the translation of said transcriptional unit, wherein said translation initiation region consists of the sequence of SEQ ID NO: 2, whereas said translation initiation region is operably linked to said nucleic acid sequence.

3. The vector of claim 1, wherein said prokaryotic signal sequence is selected from signal peptides of periplasmic binding proteins for sugars, amino acids, vitamins and ions.

4. The vector of claim 1, wherein said transcriptional unit further comprises a transcription termination region which is the rrnB transcriptional terminator sequence.

5. The vector of claim 1, wherein said nucleic acid sequence encodes a Fab.

6. The vector of claim 5, wherein both the heavy and light chains of said Fab fragment are encoded by a dicistronic transcriptional unit, and wherein each chain is operably linked to a signal sequence and an identical translation initiation region, and wherein the signal sequences and translation initiation regions are upstream of the initiation point of the translation of said transcriptional unit.

7. The vector of claim 1, wherein said promoter and said operably linked transcriptional unit comprises SEQ ID NO: 3 or a sequence complementary thereof.

8. The vector of claim 1, wherein said promoter and said operably linked transcriptional unit comprise SEQ ID NO: 4, or a sequence complementary thereof.

9. The vector of claim 1, wherein said vector is an autonomously or self-replicating plasmid, a cosmid, a phage, a virus or a retrovirus.

10. An isolated and purified nucleic acid sequence expressible in a prokaryotic host comprising the melAB promoter of the melibiose operon operably linked to a transcriptional unit comprising a nucleic acid sequence encoding an antibody and a prokaryotic signal sequence operably linked to said nucleic acid sequence, wherein the expression of said nucleic acid sequence is controlled by said melAB promoter, wherein said melAB promoter is deficient in the CRP1 binding site and wherein said melAB promoter consists of SEQ ID NO: 1 or a sequence complementary thereof.

11. The isolated and purified nucleic acid sequence of claim 10, wherein said promoter and said operably linked transcriptional unit comprises SEQ ID NO: 3 or a sequence complementary thereof.

12. The isolated and purified nucleic acid sequence of claim 10, wherein said promoter and said operably linked transcriptional unit comprises SEQ ID NO: 4 or a sequence complementary thereof.

13. A prokaryotic host transformed with the vector of claim 1.

14. A prokaryotic host transformed with the isolated and purified nucleic acid sequence of claim 10.

15. A method for producing a polypeptide in a host, comprising the steps of:
   a) constructing a vector of claim 1,
   b) transforming a prokaryotic host with said vector,
   c) allowing expression of said polypeptide in a cell culture system under suitable conditions, and
   d) recovering said polypeptide from the cell culture system.

16. The method of claim 15, whereas the polypeptide produced is a Fab fragment, whereas heavy and light chains of the Fab fragment are expressed in said cell culture system in equal amounts.

* * * * *

UNITED STATES PATENT AND TRADEMARK OFFICE
CERTIFICATE OF CORRECTION

PATENT NO. : 8,735,099 B2  
APPLICATION NO. : 13/064928  
DATED : May 27, 2014  
INVENTOR(S) : Johann Brass, Joachim Klein and Ralf Ostendorp Page 1 of 2

It is certified that error appears in the above-identified patent and that said Letters Patent is hereby corrected as shown below:

IN THE SPECIFICATION:

Column 10, Line 8
  Now reads: "Pearson & Render"
  Should read: "Pearson & Reanier"

Column 10, Line 11
  Now reads: "RNA 1"
  Should read: "RNA I"

Column 16, Line 36
  Now reads: "pip promoters"
  Should read: "prp promoters"

Column 17, Line 19
  Now reads: "ClaI/AfII"
  Should read: "ClaI/AflI"

Column 18, Line 46
  Now reads: "to The L-rhamnose"
  Should read: "The L-rhamnose"

Signed and Sealed this
Ninth Day of September, 2014

Michelle K. Lee
*Deputy Director of the United States Patent and Trademark Office*

Column 23, Line 23-24

Now reads: "(Iron CR dicitrate-binding periplasmic protein precursor"

Should read: "(Iron (III) dicitrate-binding periplasmic protein precursor"

Column 25, Line 54-55

Now reads: "and 310 by BSSHI/HindIII"

Should read: "and 310 bp BSSHI/HindIII"

UNITED STATES PATENT AND TRADEMARK OFFICE
CERTIFICATE OF CORRECTION

PATENT NO. : 8,735,099 B2  
APPLICATION NO. : 13/064928  
DATED : May 27, 2014  
INVENTOR(S) : Johann Brass, Joachim Klein and Ralf Ostendorp Page 1 of 1

It is certified that error appears in the above-identified patent and that said Letters Patent is hereby corrected as shown below:

ON THE TITLE PAGE:

Item (73)

Now reads: "Morphosys Ag, Martinsried/Planegg (DE)"

Should read: "Lonza Ag, Münchensteinerstrasse (CH) and Morphosys Ag, Martinsried/Planegg (DE)"

Signed and Sealed this
Eighteenth Day of November, 2014

Michelle K. Lee
*Deputy Director of the United States Patent and Trademark Office*